United States Patent
Huang

(10) Patent No.: US 9,433,346 B2
(45) Date of Patent: Sep. 6, 2016

(54) CIRCULAR PREFERENTIAL HYPERACUITY PERIMETRY VIDEO GAME TO MONITOR MACULAR AND RETINAL DISEASES

(71) Applicant: ICHECK Health Connection, Inc., Portland, OR (US)

(72) Inventor: David Huang, Portland, OR (US)

(73) Assignee: GOBIQUITY, INC., Dover, DE (US)

( * ) Notice: Subject to any disclaimer, the term of this patent is extended or adjusted under 35 U.S.C. 154(b) by 0 days.

(21) Appl. No.: 14/663,098

(22) Filed: Mar. 19, 2015

(65) Prior Publication Data

US 2015/0190048 A1 Jul. 9, 2015

Related U.S. Application Data

(63) Continuation-in-part of application No. 13/683,641, filed on Nov. 21, 2012, now Pat. No. 9,039,182.

(60) Provisional application No. 61/562,343, filed on Nov. 21, 2011.

(51) Int. Cl.
*A61B 3/02* (2006.01)
*A61B 3/00* (2006.01)
*A61B 3/032* (2006.01)
(Continued)

(52) U.S. Cl.
CPC ............. *A61B 3/032* (2013.01); *A61B 3/0033* (2013.01); *A61B 3/0091* (2013.01); *A61B 3/024* (2013.01); *A61B 3/028* (2013.01); *A61B 3/0041* (2013.01)

(58) Field of Classification Search
USPC ................................................ 351/239, 241
See application file for complete search history.

(56) References Cited

U.S. PATENT DOCUMENTS

| 4,989,968 A | 2/1991 | Freedman |
| 4,995,717 A | 2/1991 | Damato |

(Continued)

FOREIGN PATENT DOCUMENTS

| EP | 2048615 A1 | 4/2009 |
| KR | 100387356 | 8/2003 |

(Continued)

OTHER PUBLICATIONS

American Academy of Pediatrics; Red Reflex Examination in Neonates, Infants, and Children; Pediatrics (Journal); Dec. 2008; vol. 122, No. 6; pp. 1401-1404; US.

(Continued)

*Primary Examiner* — Jack Dinh
(74) *Attorney, Agent, or Firm* — George C. Rondeau, Jr.; Davis Wright Tremaine LLP

(57) ABSTRACT

Systems and methods for providing a video game to map macular visual acuity comprising a test where a fixation point is ensured by brief simultaneous presentation of central and pericentral targets. The game may be implemented on a hardware platform including a video display, a user input device, and a video camera. The camera is used to monitor ambient light level and the distance between the device and the eyes of the test subject. The game serves as a macular acuity perimeter that produces a map of the acuity of an eye that may be compared with normative data. The type of acuity tested is preferably Vernier acuity, but resolution acuity can also be tested. The test results are transmitted to a health care professional by telecommunications means to facilitate the diagnosis or monitoring of age-related macular degeneration or other relevant eye diseases.

36 Claims, 27 Drawing Sheets

(51) Int. Cl.
  A61B 3/024 (2006.01)
  A61B 3/028 (2006.01)

(56) References Cited

U.S. PATENT DOCUMENTS

| | | |
|---|---|---|
| 5,502,520 A | 3/1996 | Cibis et al. |
| 5,565,949 A | 10/1996 | Kasha, Jr. |
| 5,886,770 A | 3/1999 | Damato |
| 5,920,375 A | 7/1999 | Fahle et al. |
| 5,946,075 A | 8/1999 | Horn |
| 5,989,194 A | 11/1999 | Davenport |
| 6,089,715 A | 7/2000 | Hoover |
| 6,364,486 B1 | 4/2002 | Ball et al. |
| 6,523,954 B1 | 2/2003 | Kennedy |
| 6,592,223 B1 | 7/2003 | Stern et al. |
| 6,616,277 B1 | 9/2003 | Davenport |
| 6,663,242 B1 | 12/2003 | Davenport |
| 6,808,267 B2 | 10/2004 | O'Neil et al. |
| 7,287,857 B2 | 10/2007 | Glaser |
| 7,665,847 B2 | 2/2010 | Alster et al. |
| 7,878,652 B2 | 2/2011 | Chen |
| 7,926,943 B1 | 4/2011 | Reichow et al. |
| 2003/0020873 A1 | 1/2003 | Fink et al. |
| 2003/0085996 A1 | 5/2003 | Horiguchi |
| 2003/0169334 A1 | 9/2003 | Braithwaite et al. |
| 2005/0270386 A1 | 12/2005 | Saitoh et al. |
| 2006/0114414 A1 | 6/2006 | McGrath et al. |
| 2007/0126985 A1 | 6/2007 | Wiltberger et al. |
| 2007/0182928 A1 | 8/2007 | Sabel |
| 2008/0013047 A1 | 1/2008 | Todd et al. |
| 2008/0058655 A1 | 3/2008 | Severns |
| 2009/0059169 A1 | 3/2009 | Shimizu et al. |
| 2009/0079937 A1 | 3/2009 | Chen et al. |
| 2009/0079939 A1 | 3/2009 | Mimura |
| 2009/0153799 A1 | 6/2009 | Johns |
| 2009/0180071 A1 | 7/2009 | Fateh |
| 2009/0273758 A1 | 11/2009 | Wang et al. |
| 2010/0128222 A1 | 5/2010 | Donaldson |
| 2010/0128223 A1 | 5/2010 | Blumenthal et al. |
| 2010/0195051 A1 | 8/2010 | Murray et al. |
| 2011/0085138 A1 | 4/2011 | Filar |
| 2012/0016763 A1 | 1/2012 | Kirschner |
| 2013/0155376 A1 | 6/2013 | Huang |
| 2013/0235346 A1 | 9/2013 | Huang |

FOREIGN PATENT DOCUMENTS

| | | |
|---|---|---|
| WO | 2008005848 | 1/2008 |
| WO | 2010132304 | 11/2010 |
| WO | 2010132304 A1 | 11/2010 |

OTHER PUBLICATIONS

American Academy of Pediatrics; American Association of Pediatric Ophthalmology and Strabismus, and the American Academy of Ophthalmology; Eye Examination in Infants, Children, and Young Adults by Pediatricians; Pediatrics (Journal); Apr. 2003; vol. 111, No. 4; pp. 902-907; US.
Eventov-Friedman, et al.; The Red Reflex Examination in Neonates: An Efficient Tool for Early Diagnosis of Congenital Ocular Diseases; Imaj (Journal); May 2010; vol. 12; pp. 259-261; Israel.
Roe and Guyton; The Light that Leaks; Bruckner and the Red Reflex; Survey of Ophthalmology; May-Jun. 1984; vol. 28; pp. 665-670; US.
Tongue and Cibis; Bruckner Test; Ophthalmology (Journal); 1981; vol. 88, No. 10; pp. 1041-1044; US.
Donahue et al.; Screening for Amblyogenic Factors Using a Volunteer Lay Network and the MTI PhotoScreener; Ophthalmology (Journal); Sep. 2000; vol. 107, No. 5; pp. 1637-1644; US.
Miller et al,; Comparison of Preschool Vision Screening Methods in a Population with a High Prevalence of Astigmatism; IOVS; Apr. 2001; vol. 42, No. 5; pp. 917-924; US.
Donahue et al.; Sensitivity of Photoscreening to Detect High-Magnitude Amblyogenic Factors; Journal of AAPOS; Apr. 2002; vol. 6, No. 2; pp. 86-91; US.
Chen et al.; Simulation of Eccentric Photorefraction Images; Optics Express; Mar.-Jun. 2003; vol. 11, No. 14; pp. 1628-1642; US.
Donahue et al.; Preschool Vision Screenings: what Should We be Detecting and How Should We Report It? Uniform Guidelines for Reporting Results of Preschool Vision Screening Studies; Journal of AAPOS; Oct. 2003; vol. 7, No. 5; pp. 314-316; US.
Kovtoun et al.; Calibration of Photoscreeners for Single-Subject, Contract-Induced Hyperopic Anisometropia; Journal of Pediatric Ophthalmology & Strabismus; May/Jun. 2004; vol. 41, No. 3; pp. 150-158; US.
Matta et al.; Comparison Between the PlusoptiX and MTI Photoscreeners; Arch Ophthalmol; Dec. 2009; vol. 127, No. 12; pp. 1591-1595; US.
Li et al.; The Detection of Simulated Retinoblastoma by Using Red-Reflex Testing; Pediatrics (Journal); Jul. 2010; vol. 126, No. 1; pp. 201-208; US.
Donahue et al.; US Preventive Services Task Force Vision Screening Recommendations; Pediatrics (Journal); Mar. 2011; vol. 127, No. 3; pp. 568-571; US.
Arnold et al.; Calibration and Validation of 9 Objective Vision Screeners with Contact-Lens Induced Anisometropia; Pediatric Ophthalmology and Strabismus; Mar. 2012; pp. 1-18; US.
Kaakinen, Kari; A Simple Method for Screening of Children with Strabismus, Anisometropia or Ametropia by Simultaneous Photography7 of the Corneal and the Fundus Reflexes; ACTA Ophthalmologica; Jun. 1978; vol. 57 1979; pp. 161-171; Finland.
Ellis, C.J.K.; The Pupillary Light Reflex in Normal Subjects; British Journal of Ophthalmology; 1981; vol. 65; pp. 754-759; London.
Bobier et al.; Eccentric Photorefraction: Optical Analysis and Empirical Measures; American Journal of Optometry and Physiological Optics; Feb. 1984; vol. 62, No. 9; pp. 614-620; US.
Howland et al.; Optics of Photoretinoscopy: Results from Ray Tracing; American Journal of Optometry and Physiological Optics; Feb. 1985; vol. 62, No. 9; pp. 621-625; US.
Brodie, Scott E.; Photographic Calibration of the Hirschberg Test: Investigative Ophthalmology & Visual Science; Apr. 1987; vol. 28, No. 4; pp. 736-742; US.
Campbell et al.; Effect of Monochromatic Aberrations on Photorefractive Patterns; Journal of the Optical Society of America; Aug. 1995; vol. 12, No. 8; pp. 1637-1646; Canada.
Bobier, W.R.; Geometrical Theory to Predict Eccentric Photorefraction Intensity Profiles in the Human Eye; Journal of the Optical Society of America; Aug. 1995; vol. 12, No. 8; pp. 1647-1656; Canada.
Bobier, W.R.; Slope-Based Eccentric Photorefraction: Theoretical Analysis of Different Light Source Configurations and Effects of Ocular Aberrations: Journal of the Optical Society of America; Oct. 1997; vol. 14, No. 10; pp. 2547-2556; Canada.
Preferential Hyperacuity Perimeter (PHP) Research Group; "Results of a Multicenter Clinical Trial to Evaluate the Preferential Hyperacuity Perimeter for Detection of Age-Related Macular Degeneration," The Journal of Retina and Vitreous Diseases 25:3, 296-303, 2005, Tel-Aviv, Israel.
http://www.testvision.org/decide.html, webpage print, 2012.
http://www.visionrx.com/gcheck/Register.asp?frombc=1, webpage print, 2012.
Extended European Search Report for PCT Application No. PCT/US2012/053951, mailed on Apr. 2, 2015.

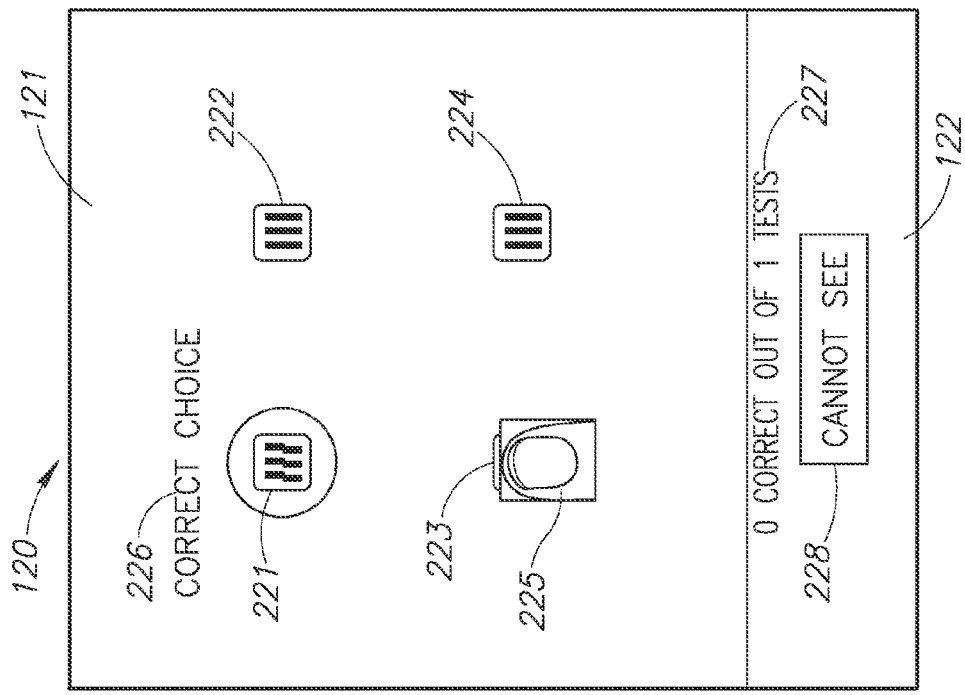
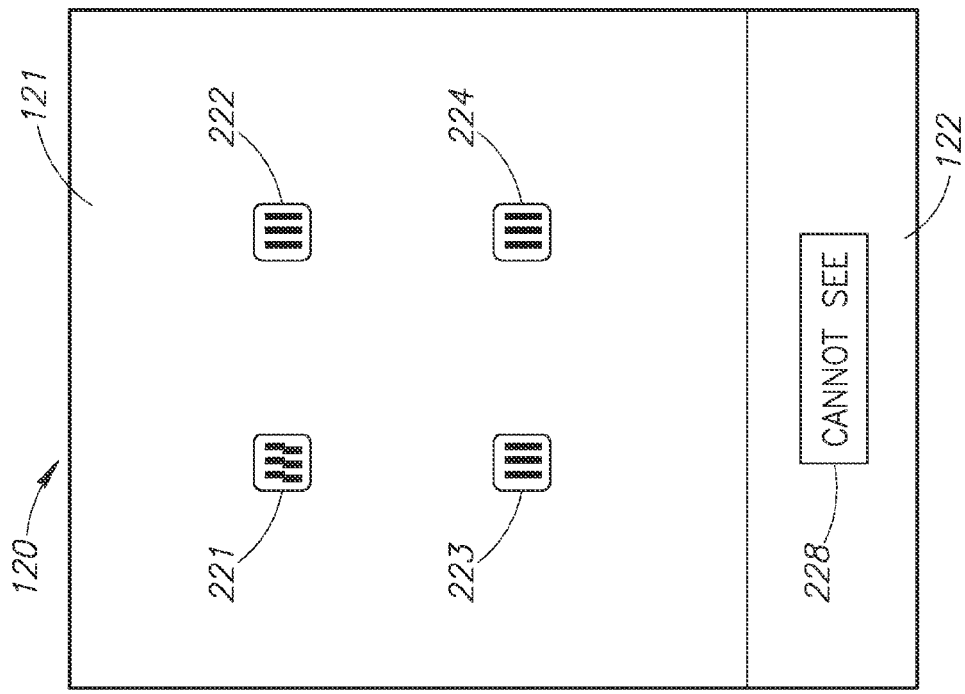

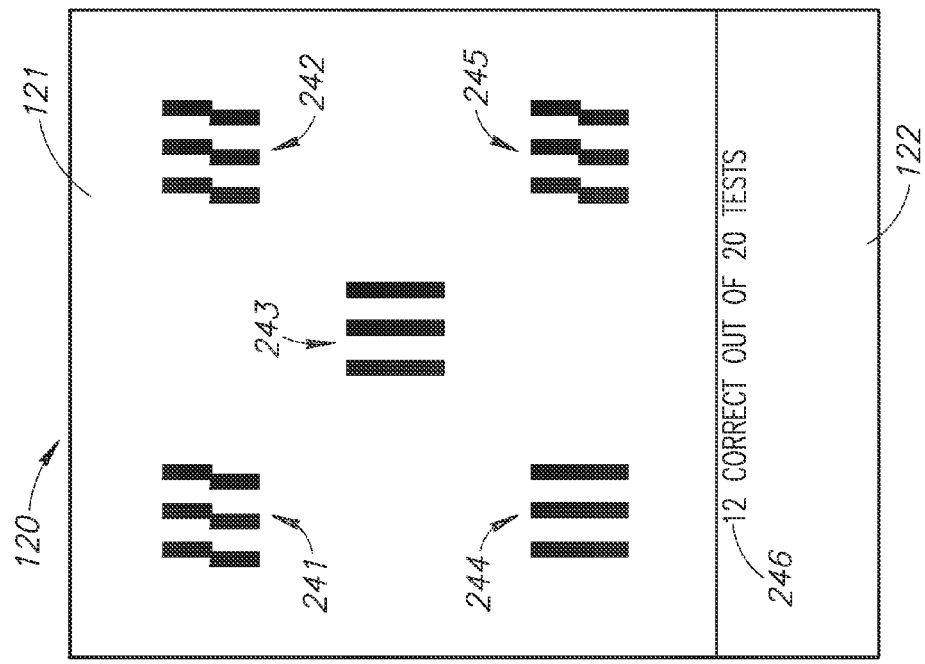
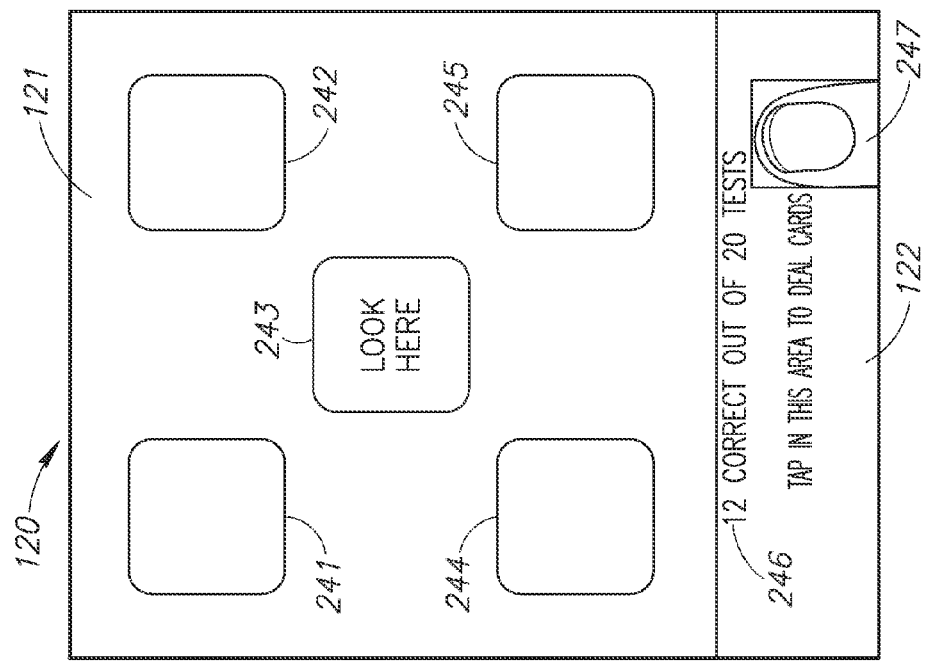

CIRCULAR PREFERENTIAL HYPERACUITY PERIMETRY VIDEO GAME TO MONITOR MACULAR AND RETINAL DISEASES

CROSS REFERENCE

This application is a continuation-in-part of U.S. application Ser. No. 13/683,641, filed Nov. 21, 2012, which claims priority to U.S. Provisional Application No. 61/562,343, filed Nov. 21, 2011, the entirety of which are incorporated herein by reference.

BACKGROUND

1. Field of the Invention

The present invention is directed generally to systems and methods for monitoring macular and retinal diseases, and more particularly to providing programs or video games for testing or mapping macular visual acuity.

2. Description of Related Art

Age-related macular degeneration (AMD) is a leading cause of blindness. It is a degeneration of the macula (central portion of the retina) that is associated with age. The progress of AMD is generally slow in the dry form of the disease. However, in a portion of affected eyes the wet form of the disease can arise, where abnormal growth of new vessels and scar tissue under the retina can lead to rapid loss of vision. The abnormal growth of new blood vessels is called neovascularization and therefore wet AMD is also called neovascular AMD. Fortunately, neovascular AMD can now be treated by intravitreal injection of anti-angiogenic medications, which often reverse the loss of vision. However, early detection of neovascular AMD is needed for treatment to begin in time before the loss of vision becomes permanent.

The Amsler chart is a long standing standard test for AMD that can detect distortions in vision caused by neovascular AMD. However, its sensitivity in detecting neovascular AMD is much lower than a newer test called the preferential hyperacuity perimeter (PHP), where the Vernier acuity of the pericentral area is mapped. Vernier acuity is defined by the resolution with which an eye can detect the relative location of two visual stimuli, such as the relative displacement of two line segments. Vernier acuity is also called hyperacuity because its threshold of perception is several times finer than the eye's ability to perceive spatial separation between features in a standard visual acuity target, such as the opening in the Landolt C or line separations in the tumbling E or standard optotypes. Compared to normal acuity, Vernier acuity is relatively unaffected by degradation of retinal image quality by cataract and other age-related conditions. Therefore it is a good test to detect retinal abnormalities in an elderly population.

Currently PHP testing is performed using a special device that is installed in the clinic of retina specialists and ophthalmologists. It is administered by trained personnel. Therefore it is not accessible to AMD patients for frequent self-testing. There is a need for home test that can be self-administered by subjects who has AMD or are at risk for AMD, so that the test can be performed frequently (daily or weekly). The test should preferably be in the form of a game that can maintain player interest. And the resulting preferential hyperacuity map should preferably be automatically analyzed by a computer and transmitted electronic to a physician who monitors the patient's eye health.

BRIEF DESCRIPTION OF THE DRAWINGS

FIG. 7 illustrates a third screen shot of the flash card game measuring central acuity in accordance with an embodiment;

FIG. 8 illustrates a fourth screen shot of the flash card game measuring central acuity in accordance with an embodiment;

FIG. 13 illustrates a first screen shot of the flash card game measuring perifoveal vision in accordance with an embodiment;

FIG. 14 illustrates a second screen shot of the flash card game measuring perifoveal vision in accordance with an embodiment;

DETAILED DESCRIPTION OF THE INVENTION

Embodiments of the present invention are useful for the detection and monitoring of retinal diseases affecting primarily the macula. There are many such diseases, but the most common ones are age-related macular degeneration (AMD) and diabetic retinopathy.

Generally, embodiments of the present invention include a video game or program configured to map macular visual acuity comprising a multiple choice test wherein a fixation point is ensured by brief, simultaneous presentation of both a central and pericentral targets. The game is implemented on a hardware platform comprising a video display, a user input device, and an image or video camera. The camera is used to monitor ambient light level, and to monitor the distance between the device and the eyes of the test subject. The game serves as a macular acuity perimeter that produces a map of the acuity of an eye that may be compared with normative data. The type of acuity tested is preferably Vernier acuity (also called "hyperacuity"), but resolution acuity or other types can also be tested.

The test is suitable to be self-administered by the user (also referred to as the player or the subject herein) with or without professional supervision. The results may be transmitted (e.g., wirelessly) to a health care professional by telecommunications means to facilitate the diagnosis or monitoring of age-related macular degeneration or other relevant eye diseases. Embodiments of the present invention are sometimes referred to herein as the macular acuity perimetry (MAP) test.

First Embodiment

Embodiments of the present invention include a computer with a video monitor, a video camera, and a human-user input device. One example of an integrated apparatus serving these functions is the iPad 2® (Apple Inc., Cupertino, Calif.). Other computers or computer systems with similar functionalities may also be used.

Figure 1:
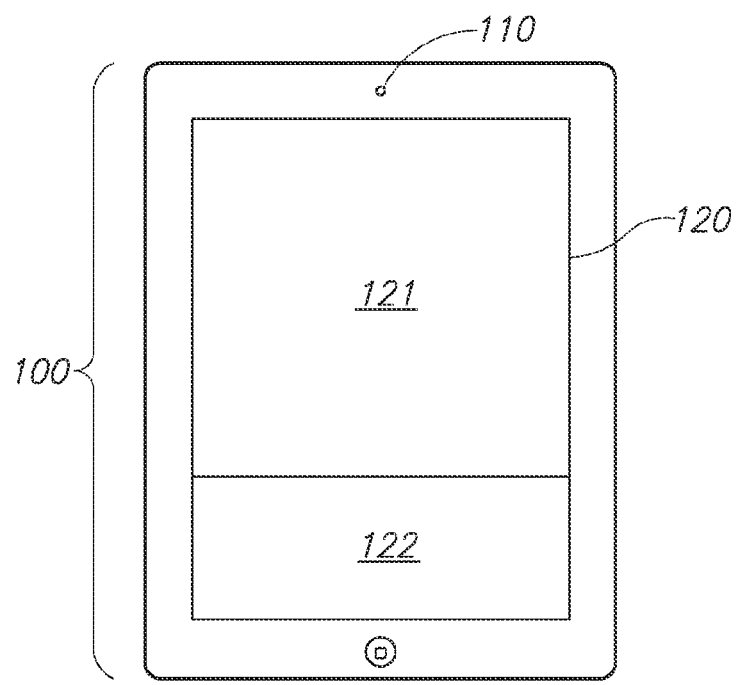
FIG. 1 illustrates a display, input device, and distance-monitoring camera features of an embodiment of the invention implemented using a tablet computer.

Referring to FIG. 1, a device 100 is shown that has a video camera 110 configured to monitor the distance between the device and a test subject's eyes. The device 100 also comprises a touch screen display 120 that is divided into a main game play area 121 and an ancillary area 122. The play area 121 is used to display the visual action of a game. The play area 121 is preferably approximately square, but other shapes may also be used. The ancillary area 122 is used as an ancillary human-user input and score display, as discussed below.

Figure 2:
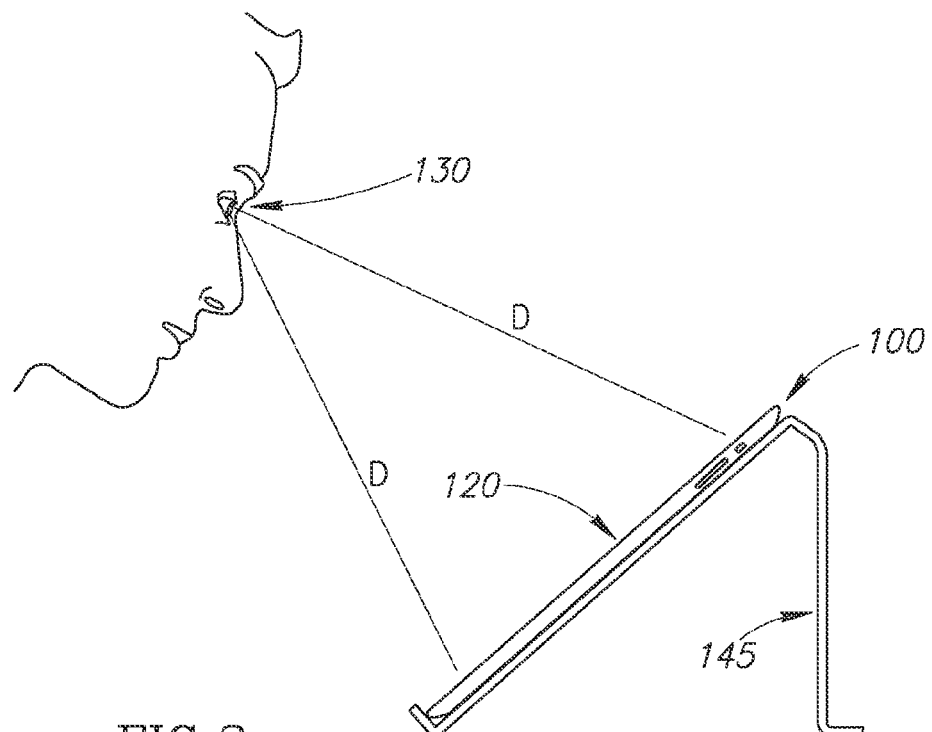
FIG. 2 illustrates the operation of an ambient light monitoring camera and a viewing stand according to an embodiment of the present invention.

Referring to FIG. 2, the device 100 may be positioned on a stand 145 such that the user's eye 130 is approximately equal distance (D) to the top and bottom of the device's display 120. The camera 110 on the front of the device 100 is used to monitor ambient light. The test is preferably performed in dim room lighting (low scotopic). The brightness of the screen 120 may be automatically adjusted according to the ambient light level within an acceptable range. Outside of the acceptable range, a warning message on the screen 120 may be provided to instruct the user to increase or decrease the room lighting appropriately.

Figures 3A, 3B:
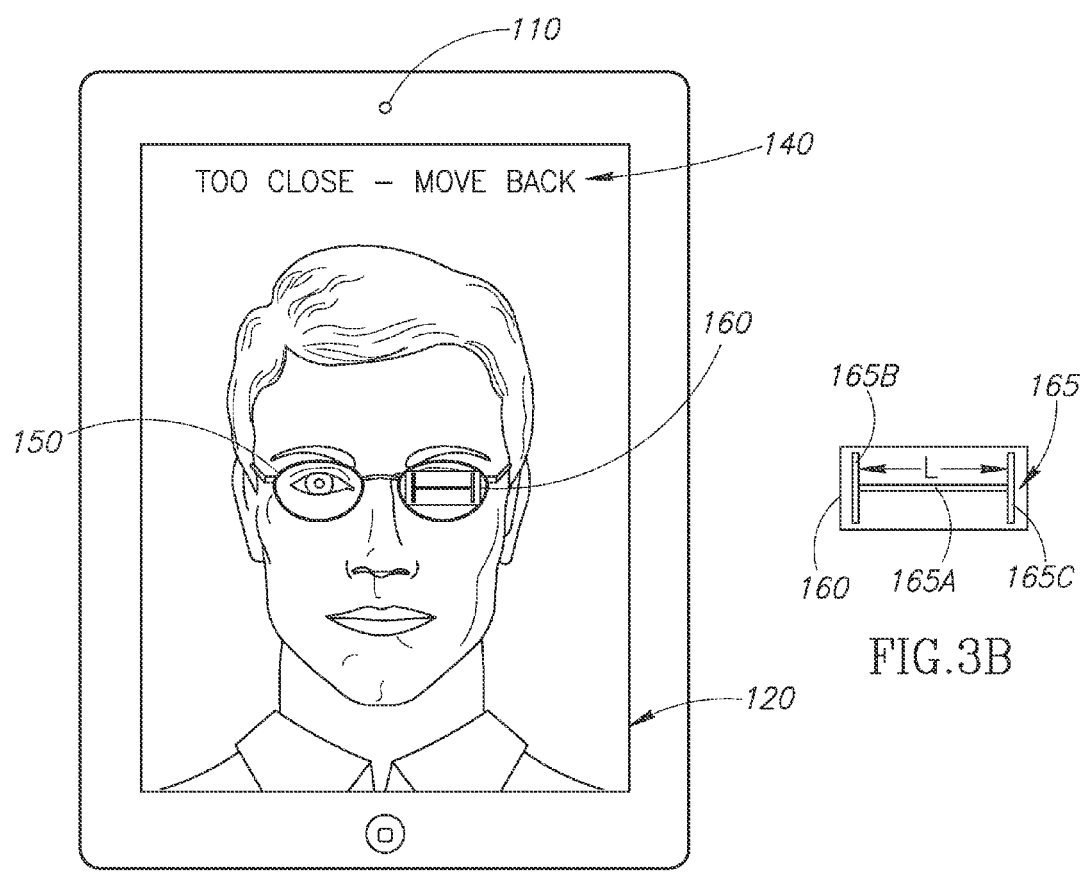
FIG. 3A illustrates the operation of a distance adjustment process using video analysis of a pattern printed onto an eye occluder.
FIG. 3B illustrates an enlarged view of the eye occluder shown in FIG. 3A.

Referring to FIGS. 3A and 3B, an occluder 160 is shown that may be used to occlude vision in one eye so the other eye can be tested using the video game of the present invention. The occluder 160 could be mounted on spectacles 150 or could be fixed on the user's head using straps. The occluder 160 has a visible feature 165 of known dimensions which is captured by the video camera 110 and can be analyzed by a computer (see FIG. 4) of the device 100 to monitor the distance between subject's eyes and the device. As shown, the visual feature 165 could include, for example, a horizontal bar 165A with well-defined termination points (e.g., vertical bars 165B and 165C) so that the length of the horizontal bar may be easily determined by computerized automatic image processing. Other shapes or patterns, such as a circle or rectangle, could also be used. Based on the video analysis, the device 100 may display an instruction 140 on the screen 120 (and/or by sound) so the user can position his or her head within the optimal range of distance from the device.

Figure 3C:
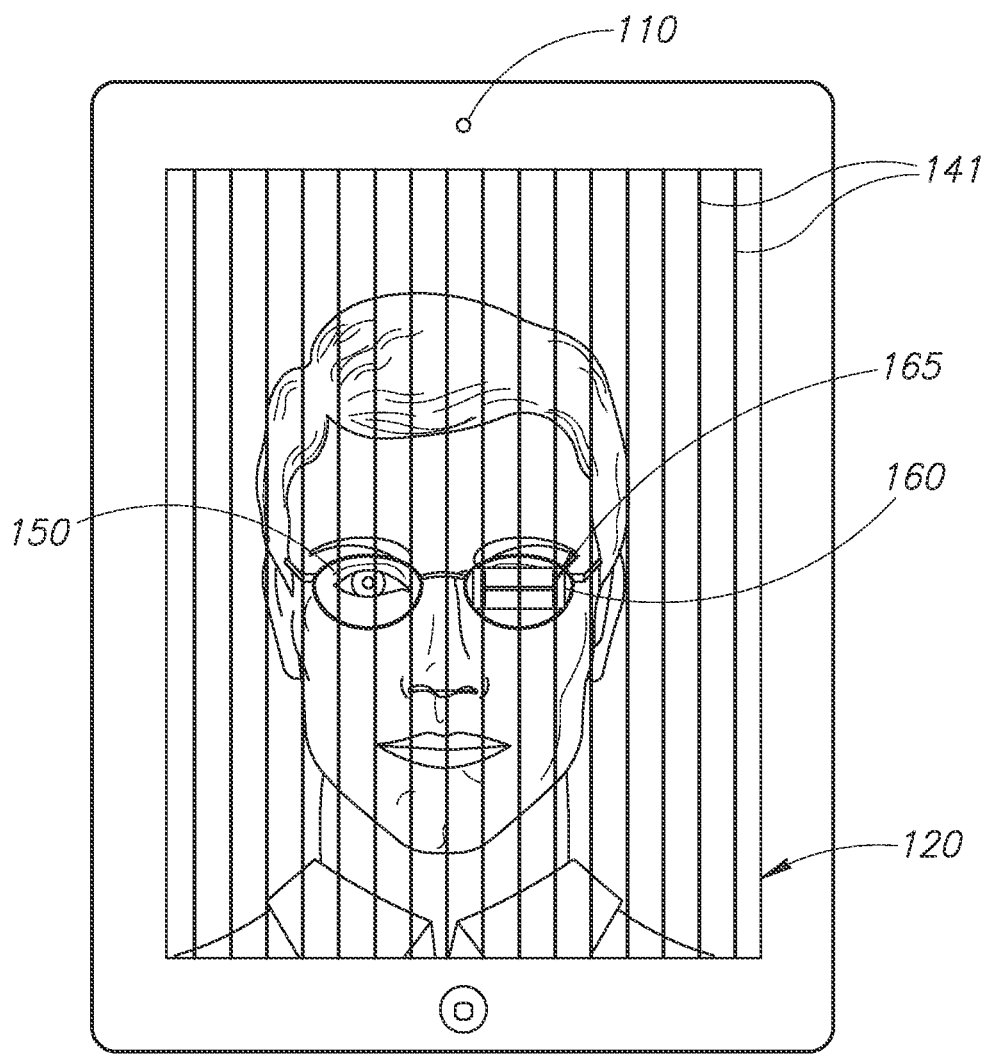
FIG. 3C illustrates the operation of a second distance adjustment process that utilizes a regularly-spaced vertical line overlay.

An alternative method, shown in FIG. 3C, of obtaining the desired viewing distance D asks the user to adjust the viewing distance until the size of the real-time video display the occluder 160 has the correct size. In the example shown, the user compares the video display of the calibration feature 165 against a regularly spaced vertical line overlay 141. The user moves his/her head and/or the device 100 back and forth until the length of the feature 165 (e.g., between vertical bars 165B and 165C) spans two interval spacing between the vertical lines 141.

Another alternative method for the device 100 to monitor viewing distance is to analyze the size of the subject's eye (e.g., corneal width from limbus to limbus) being tested or other features on the subject's face. For this alternative to work, a video frame may first be taken when the user's face is at a known distance from the camera 110. As an example, the distance could initially be established using a measuring tape or ruler with a known length.

Figure 4:
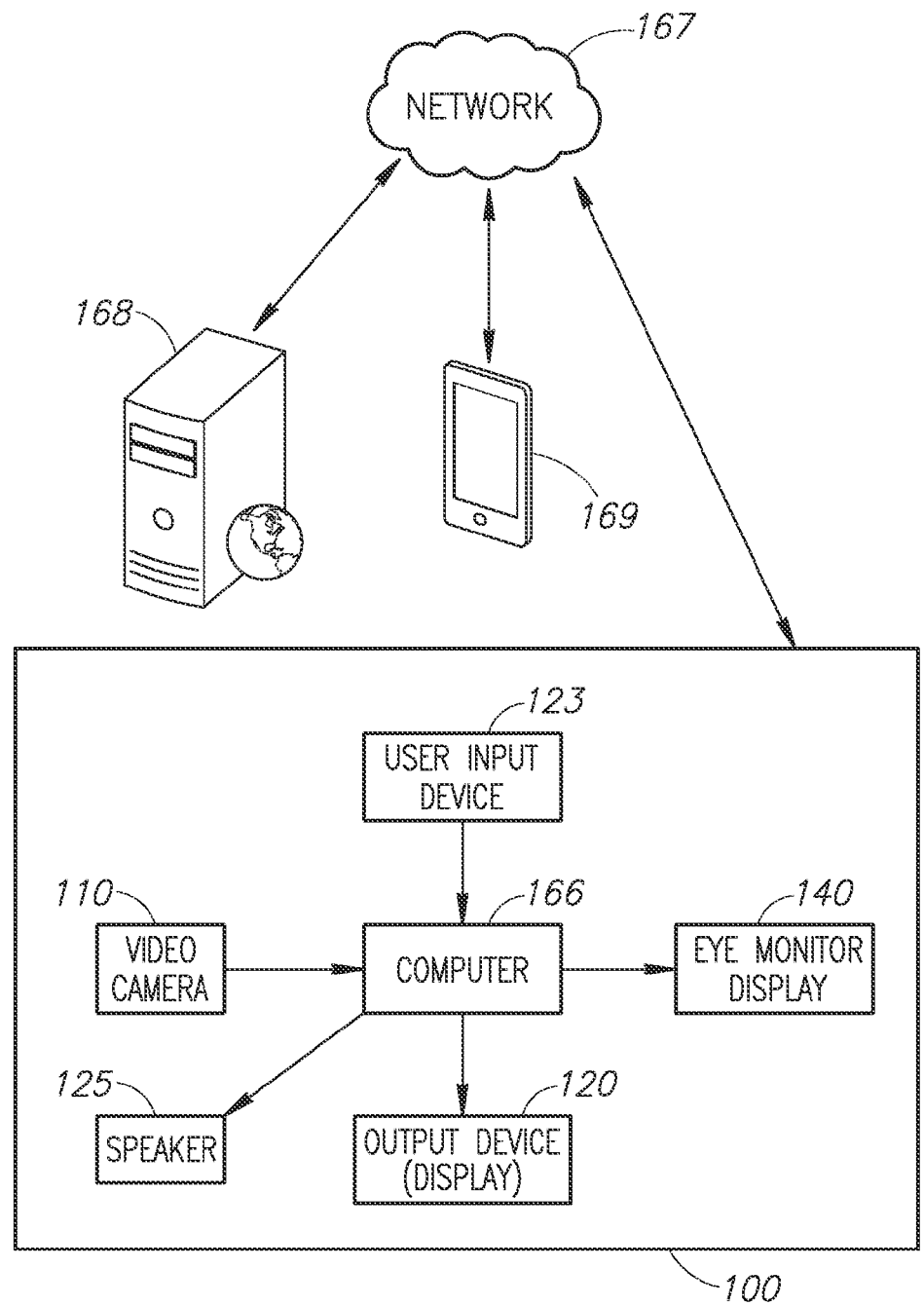
FIG. 4 is a block diagram illustrating the relationship between a computer according to an embodiment and its input and output devices.

Referring now to FIG. 4, an input device 123 and an output device 120 are shown connected to a computer 166 of the device 100. The term computer used in this instance refers to processors, memory, data/control bus, etc., as opposed to the peripheral input and output devices. The input and output functions can both be performed on the same touch screen, as depicted in FIG. 1. The video camera 110 produces image frames that are processed by the computer 166 to monitor the distance between the subject's eyes and the device 100. The subject produces action in the video game with the input device 123 and the game background and actions are displayed on the video display or output device 120. The game sounds are output on a speaker 125.

The test results may be transmitted or uploaded (e.g., wirelessly) to a server 168 over a network 167 (e.g., the Internet, a mobile communications network, etc.). This feature allows for the storage, tracking, review, and analysis of the test results over time to detect patterns, such as the deterioration of a patient's vision. The patient, his or her healthcare professionals, or others may access the data stored on the server 168 through a web browser or via a link to an electronic health record system of a healthcare facility. The test results data may be processed and presented in a manner that is useful for the patient and/or healthcare provider to analyze the results.

The server 168 may also be configured to provide notifications or alerts to the patient or their healthcare provider for any changes in vision that may require further attention or treatment. These alerts may be sent to a patient's and/or healthcare provider's electronic devices (e.g., the mobile phone 169) via email, SMS messages, voice messages, or any other suitable messaging system. For example, if an analysis of the uploaded test results reveals that a patient's vision is deteriorating, the server 168 may automatically send a message to the patient and/or a healthcare provider to alert them of the change in condition. Thus, appropriate action or treatment may be provided.

Initial Setup

The user is instructed to perform the setup steps by the device 100 without the need of human professional instruction and supervision, though a human supervisor could be helpful to assure proper use.

The first time the subject is taking the test, the subject's identifying information (e.g., name, age, etc.) may be entered into the computer 166 using the user input interface 123. An acuity map of a normal population may be used as the initial estimate of the subject's acuity map. For subsequent tests, the initial estimate may be the average of the subject's recent tests.

Since a game is used to perform the MAP test, the terms "game" and "test" are used interchangeably herein. Further, the user of the device 100 is the subject of the MAP test and the game player. Therefore, the terms "user," "subject," and "player" are also used interchangeably.

Before and/or during each game, the brightness of the screen 120 may be adjusted to the desired range by the use of the camera 110 (see FIG. 1) as described above. If the ambient light detected by the camera 110 is too high or low to be compensated for by adjusting the brightness, a message may be displayed on the display area 121 so the user can adjust the light level in the room. The test should generally be administered with the light level in the low scotopic range.

The test is administered at a viewing distance that is sufficient to provide useful AMD diagnostic information. For example, the iPad 2® used in some embodiments has a screen that is 5.8 inches wide. Referring back to FIG. 1, the display area 121 uses this full width of the screen. This provides a maximum perimetry testing area of 18 degrees full width at a viewing distance of 18 inches, using the methods of the current invention. As discussed above, the device 100 monitors the viewing distance D by taking images of the user's face (see FIG. 3) using the camera 110. The computer 166 (see FIG. 4) analyzes the visible feature 165 on the occluder 160 to compute the distance between the camera 110 and the occluder 160, which is approximately the same as the viewing distance. At the setup of each game, the device 100 instructs the user to move his or her head into position so the image of their face (in particular, the occluder 160) can be captured by the camera 110 and displayed in display area 121. The device 100 then instructs the user to move closer to or further from the display area 121 to bring the user's eyes into the target range of viewing distance. The initial target range may be 17 to 19 inches, for example.

Generally, the user should be wearing spectacle correction for their best vision within the operating range of the viewing distance. For an emmetrope, a pair of reading glasses with power of +2.25 D would be optimal for the viewing distance of 18 inches. If spectacles are used, the occluder 160 should be mounted over the spectacle lens over the eye not being tested. If no spectacles are needed or if the subject is using contact lenses, the occluder 160 could be mounted over plano glasses or strapped on as an eye patch.

Game Playing and Perimetry Test Cycle

Many game scenarios could be devised based on the principles of the current invention. For the purpose of demonstration, an exemplary flash card multiple-choice game illustrated in FIGS. 5-20 is described.

Figure 5:
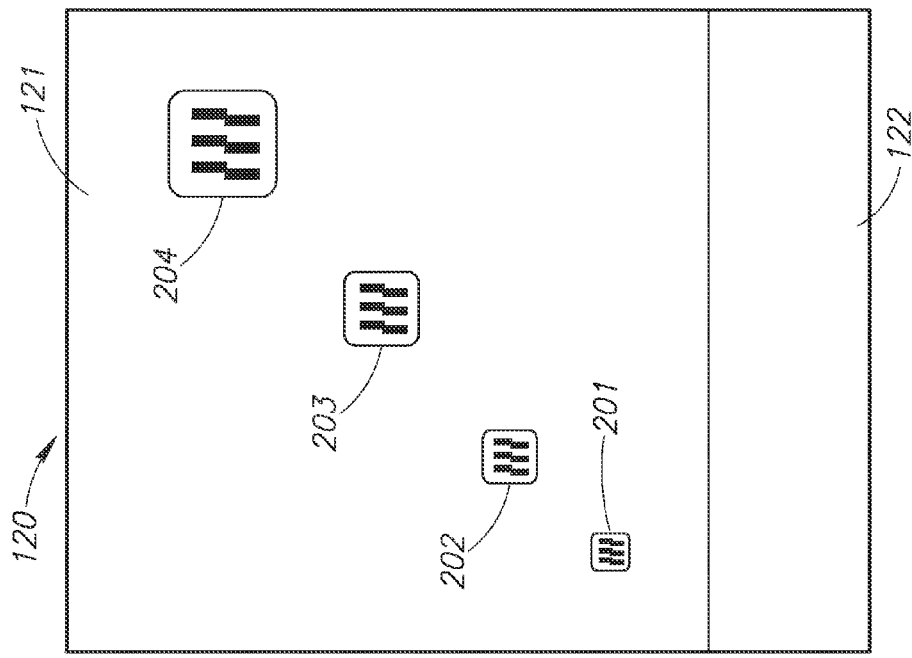
FIG. 5 illustrates a first screen shot of a flash card game measuring central acuity in accordance with an embodiment.
Figure 6:
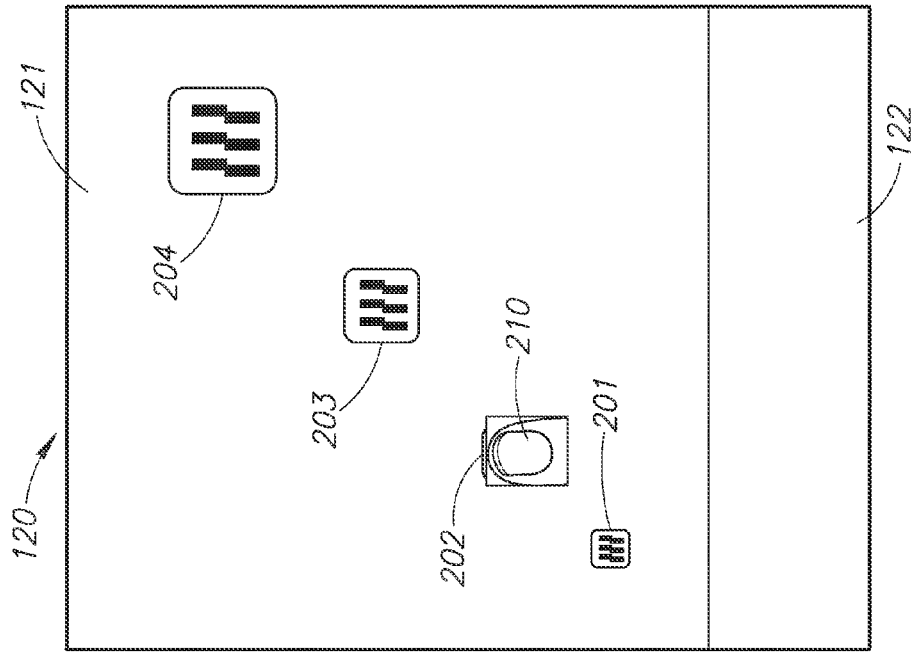
FIG. 6 illustrates a second screen shot of the flash card game measuring central acuity in accordance with an embodiment.

The initial rounds of the game are used to establish central visual acuity. This is done using several rounds of "open card" games. Referring to FIG. 5, the display area 121 has a uniform background (e.g., a green background) with a number of open cards 201-204 thereon displaying visual acuity targets over a range of sizes bracketing around the user's estimated central acuity. Vernier acuity targets are preferably used, though normal acuity targets can also be employed. Vernier acuity targets test relative displacements such as relative shifts between two groups of line segments, as shown by the cards 201-204 in FIG. 5. A single line can also be used instead of multiple lines. Other types of unevenness or distortions in a straight line, curve, or circle can also be used. In an opening round, the subject selects the smallest card 201-204 on which he (or she) can perceive the shift between line segments by tapping on the touch screen 120 with a finger 210, as shown in FIG. 6. The visual angle subtended by the spatial shift defines the Vernier acuity.

The selected acuity level is then confirmed and refined using a multiple-choice test. Referring to FIG. 7, four open cards 221-224 each showing the same size target are displayed. The player is tasked to select the one card of the cards 221-224 that is different from the other cards. In this example, the card 221 has a lateral shift between the line segments, while the other three cards 222-224 have no shift (aligned). For the sake of brevity, cards with shifted line segments are referred to as "shifted" cards and card with the aligned line segments are referred to as "aligned" cards. The test asks the subject to pick out the one card that is different from the other cards. Thus, the test could involve one shifted card and several aligned cards, or one aligned card and several shifted cards. A greater or smaller numbers of cards (for example, 2, 3, or 9 cards) could also be used.

Referring to FIG. 8, the subject chooses the one of the card 221-224 he believes is different from the other cards by tapping on the card on the touch screen 120 with a finger 225. In this example, the choice was wrong and therefore the device 100 displays the correct choice with a message 226 and displays a score 227 saying "0 correct out of 1 test." If the subject cannot see the patterns on the card, then the subject should tap on a "cannot see" button 228 rather than tap on the wrong choice. This should be explained in the game instructions so the test may proceed faster. After a brief delay, a new round of the game is started with a display similar to that shown in FIG. 7, but with a new set of cards where the location and type (shifted versus aligned lines) of the correct choice is different (e.g., randomly selected, etc.). In some embodiments, the central acuity level is established when the player chooses a sufficient number of correct cards at a certain error level (e.g., a 5% error level—the probability of achieving equal or greater number of correct choices being less than 5%).

Given a choice of four cards each round and allowing for zero selection error, the subject needs to make the correct choice in three rounds of the game to establish that he was able to perceive the correct choice at the acuity level being displayed. If this occurs, then the acuity level is raised (i.e., the lateral shift is made smaller) and more rounds of games are played until the user's perception is established or refuted. If the player clicks the "cannot see" button 228 (see FIG. 8) or makes the correct choice in only one of three rounds, then perception is refuted. If he make the correct choice in two of three rounds (a borderline case), then one additional round is played for a total of four rounds. If the player makes the correct choice in three of four rounds, then perception is established. If he made the correct choice in two of four rounds, then perception is refuted. Thus for a choice of four cards per round, three rounds are played if the player makes no error and four rounds are played if the player makes one error. For a choice of fewer cards, a larger number of rounds are needed. The numbers of test rounds needed are tabulated in Table 1 shown below.

TABLE 1

The number of test rounds needed to establish perception at <5% error level.

| # of choices | # allowed wrong 0 | 1 |
|---|---|---|
| 2 | 5 | 8 |
| 3 | 3 | 5 |
| 4 | 3 | 4 |
| 9 | 2 | 3 |

Table 1 is calculated based on the following equations on the condition that $P_{y \leq Y} < 5\%$.

$$P_C(x) = \frac{n! \left(\frac{1}{c}\right)^x \left(1 - \frac{1}{c}\right)^{n-x}}{x!(n-x)!} \quad \text{Equation 1}$$

$$P_{y \leq Y} = \sum_{x=n-Y}^{n} P_C(x) \quad \text{Equation 2}$$

where $P_C(x)$ is the probability of the number of correct choices being arrived at by random chance, x is the number of rounds in which the correct card was picked, n is the total number of rounds played, c is the number of cards to choose from in each round, $P_{y \leq Y}$ is the probability that $y \leq Y$ by random chance, y is the number of rounds in which the wrong card was picked, and Y is the number of wrong choices allowed.

Once the central acuity is established in the initial rounds, the game proceeds to map parafoveal and perifoveal acuity. Anatomically, the fovea refers to the region approximately 1 mm in diameter, the parafovea refers to the surrounding region 2.5 mm (8 degrees) in diameter, and the perifovea the surrounding region 5.5 mm (18 degrees) in diameter. Again, Vernier acuity targets are preferred, but standard acuity targets can also be used. Preferably, a "flash card" game is used.

Figure 10:
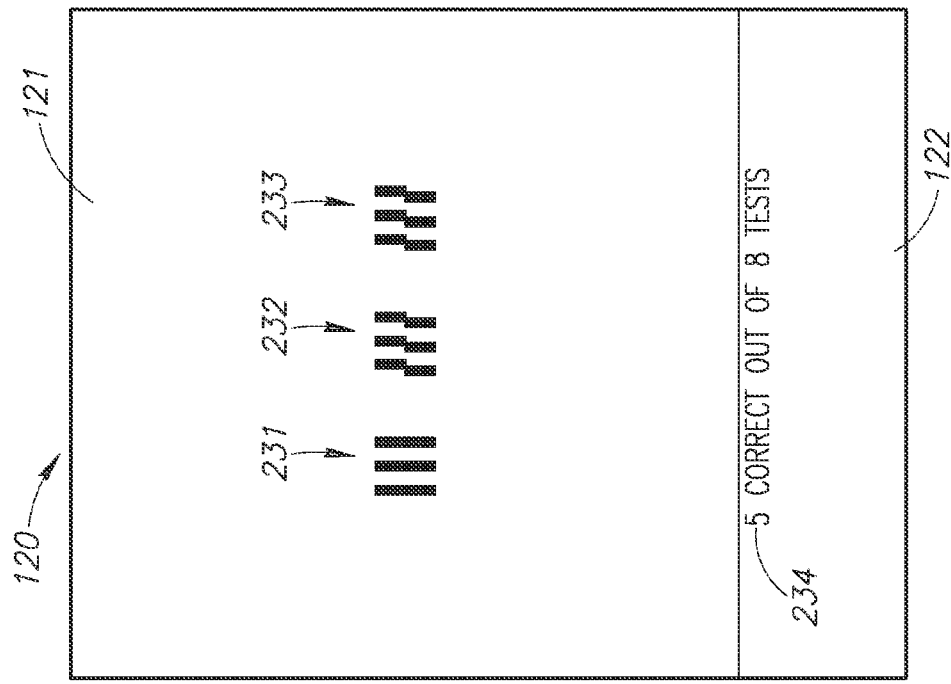
FIG. 10 illustrates a second screen shot of the flash card game measuring parafoveal acuity perimetry in accordance with an embodiment.
Figure 9:
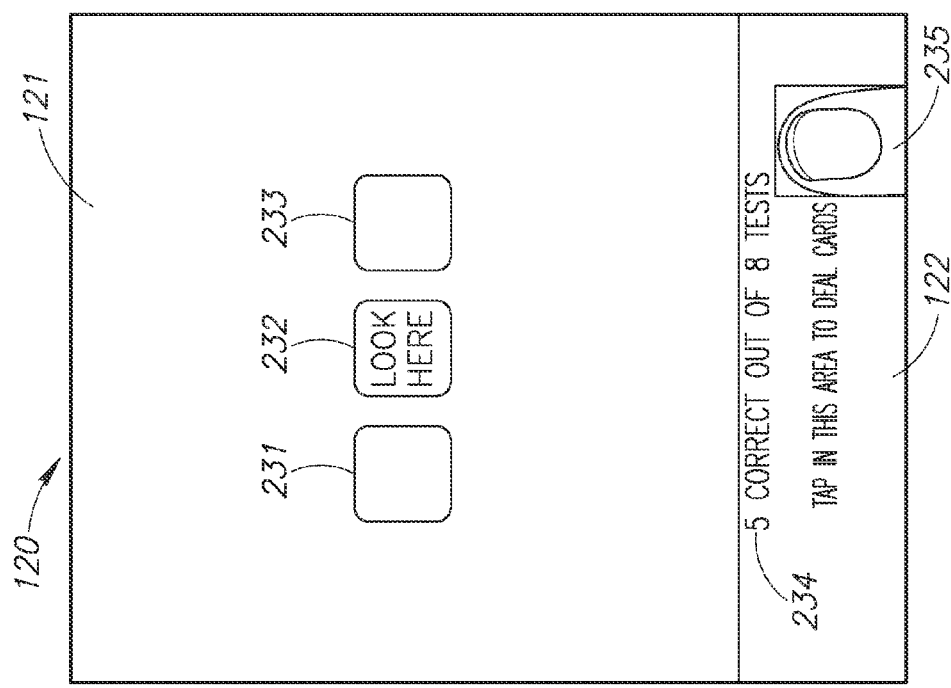
FIG. 9 illustrates a first screen shot of the flash card game measuring parafoveal acuity perimetry in accordance with an embodiment.
Figure 12:
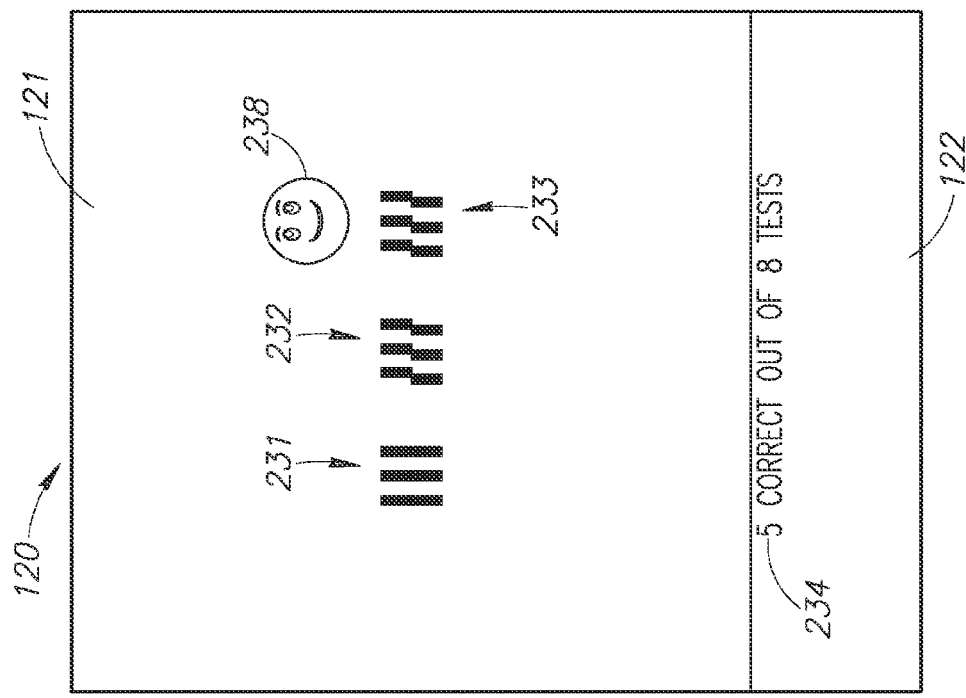
FIG. 12 illustrates a fourth screen shot of the flash card game measuring parafoveal acuity perimetry in accordance with an embodiment.
Figure 11:
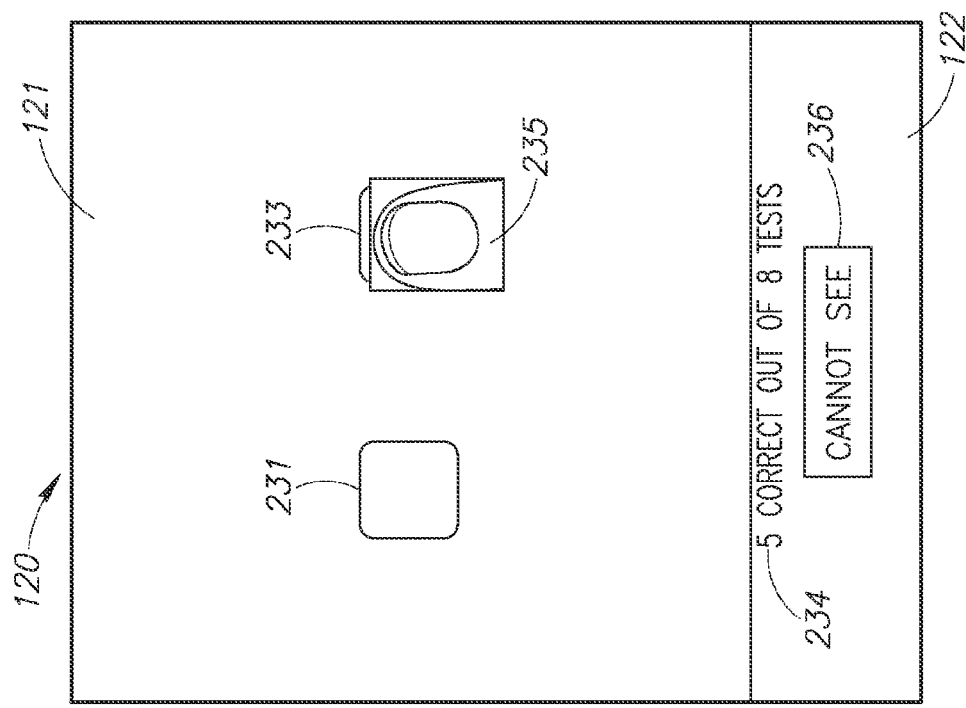
FIG. 11 illustrates a third screen shot of the flash card game measuring parafoveal acuity perimetry in accordance with an embodiment.

An example of parafoveal acuity perimetry is first described. Referring to FIG. 9, three cards 231-233 are dealt face down with their line patterns covered. A game score 234 is shown in the ancillary display area 122 to inform the player of the number of correct choices made and the number of test rounds played. The player activates a "flash reveal" (i.e., a brief display of the face of the cards) of the cards by a finger tap 235 in the display area 122. The player is asked to fixate on the central card 232 at this stage of the game. The "back" of this card may include a "fixation location indicator" (e.g., "look here") to instruct the user to fixate on the central card 232. Referring to FIG. 10, the shifted or aligned line patterns associated with cards 231-233 are revealed in a brief flash (e.g., 0.2 seconds, 0.5 seconds, etc.). The patterns on the faces of the cards 231-233 should be revealed for only a short period of time so the player does not have a chance to shift their gaze from the central card 232 to a side card 231 or 233. After a fraction of a second, the side cards 231 and 233 are once again covered to conceal the line patterns (see FIG. 11). The player is then asked to identify which of the concealed cards 231 and 233 has the same pattern as the central card 232. In this example, the player's finger tap 235 on card 233 is correct. Referring now to FIG. 12, the correct choice of the card 233 is rewarded by a smiley face icon 238 or other visual and/or sound effects. The score 234 is also updated to reflect the increase in the number of correct choices made and the number of rounds played.

FIGS. 13-16 illustrate one game round to test perifoveal vision. Referring to FIG. 13, five cards 241-245 are dealt face down. A game score 246 is shown in the display area 122 to inform the player of the number of correct choices made and the number of test rounds played. All of the cards 241-245 are dealt with the line patterns covered (i.e., face down). The player activates the flash reveal of the cards by a finger tap 247 in the area 122. The player is asked to fixate on the central card 243 at this stage of the game.

Figure 16:
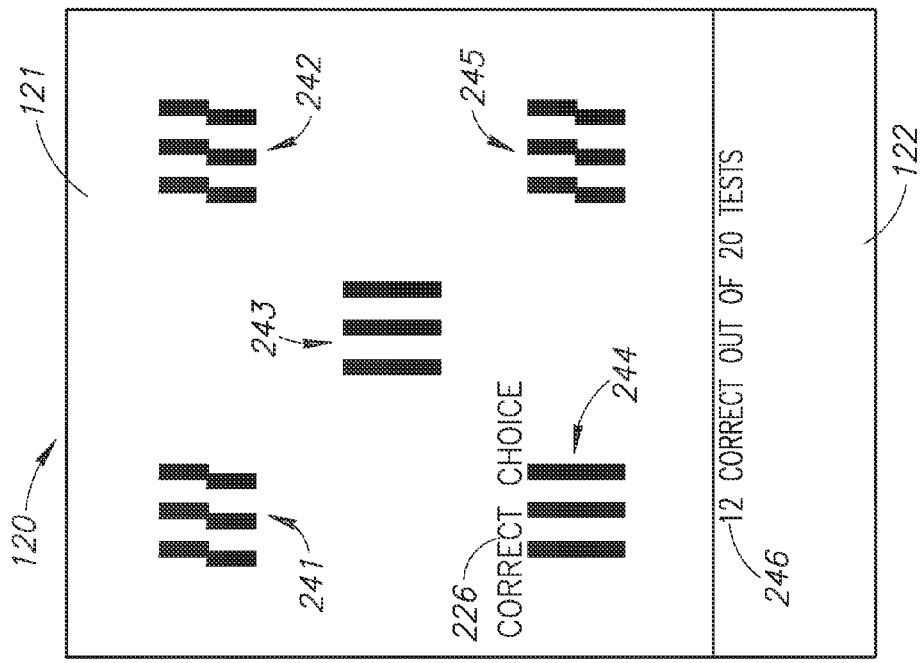
FIG. 16 illustrates a fourth screen shot of the flash card game measuring perifoveal vision in accordance with an embodiment.
Figure 15:
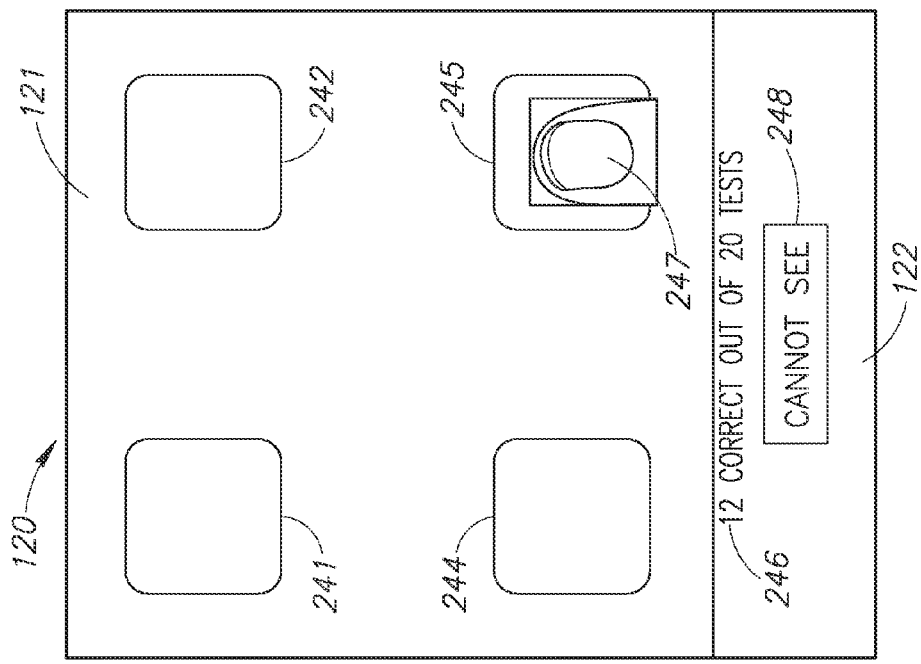
FIG. 15 illustrates a third screen shot of the flash card game measuring perifoveal vision in accordance with an embodiment.

Referring to FIG. 14, the shifted or aligned line patterns associated with cards 241-245 are revealed in a brief flash. After a fraction of a second, the edge or side cards 241, 242, 244, and 245 are again covered to conceal the line patterns (see FIG. 15). The player is then asked to identify which of the concealed cards has the same pattern as the central card 243. In this example, the player's finger tap 247 on the card 245 chooses the incorrect card. Referring now to FIG. 16, the correct card 244 is then revealed and marked as correct by an indicator 226. The score 246 is also updated to reflect the increase in the number of correct choices made and the number of rounds played. Referring back to FIG. 15, the player can make the testing go much quicker by clicking the "Cannot See" button 248 when he is not able to see the patterns on the side cards 241, 242, 244, and 245.

Figure 18:
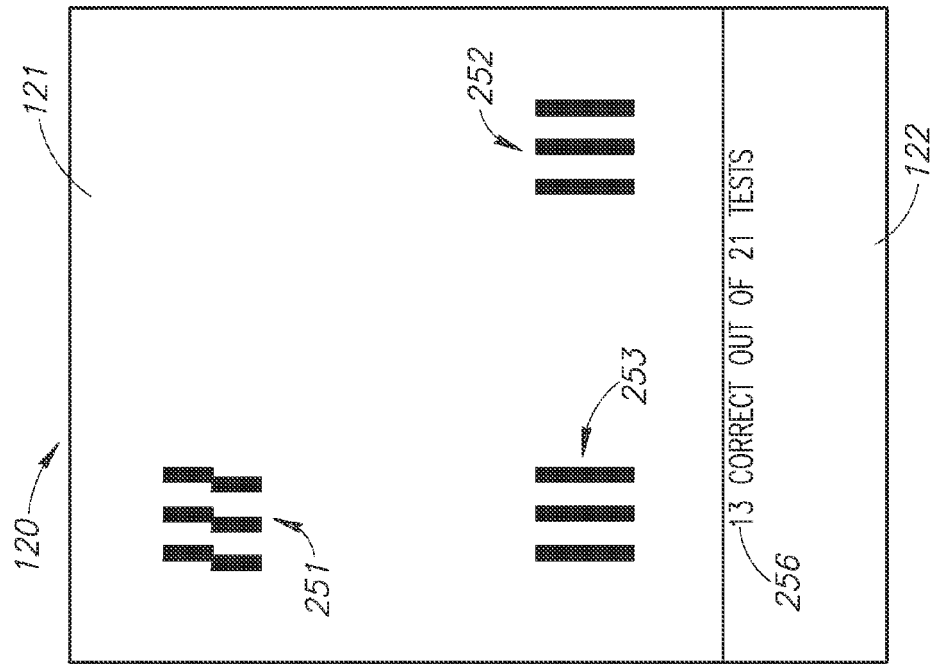
FIG. 18 illustrates a second screen shot of the flash card game measuring perifoveal vision on a small screen in accordance with an embodiment.
Figure 17:
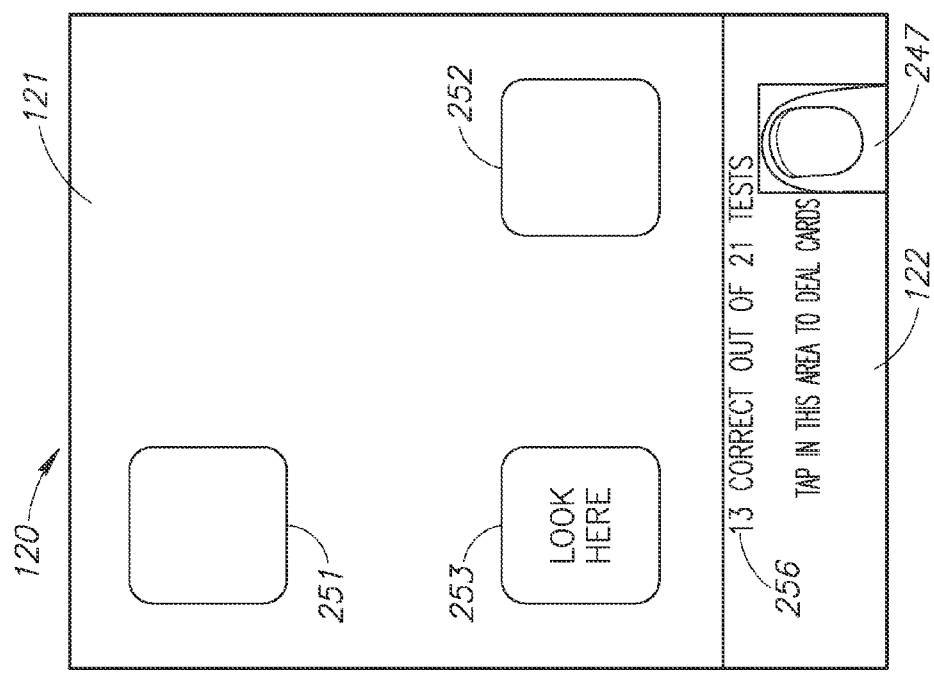
FIG. 17 illustrates a first screen shot of the flash card game measuring perifoveal vision on a small screen in accordance with an embodiment.
Figure 20:
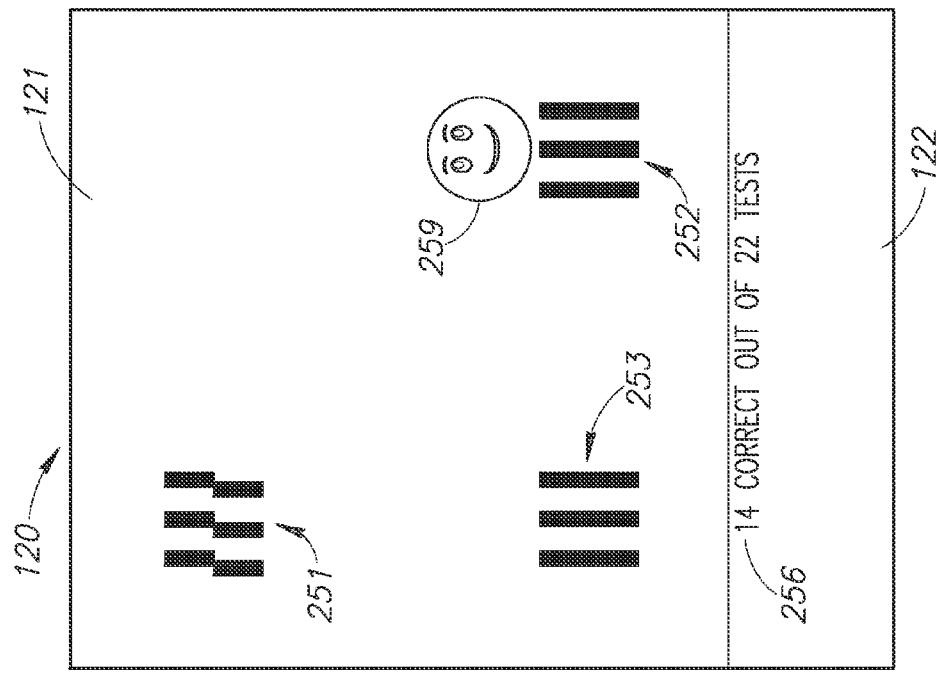
FIG. 20 illustrates a fourth screen shot of the flash card game measuring perifoveal vision on a small screen in accordance with an embodiment.
Figure 19:
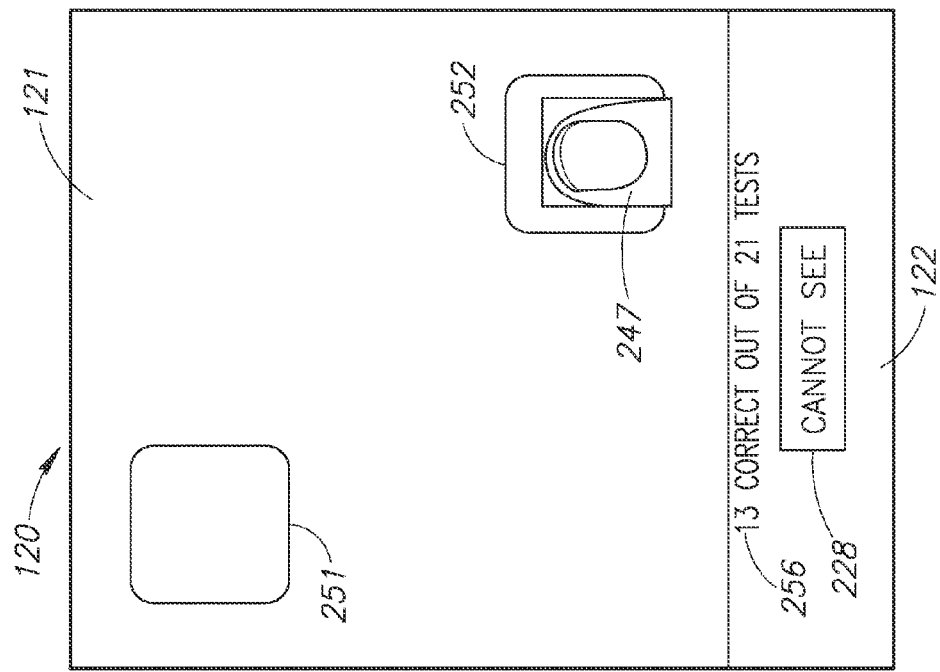
FIG. 19 illustrates a third screen shot of the flash card game measuring perifoveal vision on a small screen in accordance with an embodiment.

FIGS. 17-20 illustrate a method of testing perifoveal vision on a small screen such as on a mobile phone. For example, on a typical mobile phone with a 2 inch screen width, the visual angle subtended by the screen is only 8 degrees, even at a closer viewing distance of 14 inches. If the fixation point is placed at the center of the screen, then the screen is only large enough to test parafoveal vision (8 degrees diameter), but not perifoveal vision (18 degrees diameter). However, the testable visual field can be doubled if the fixation point is placed at the peripheral edge of the display screen. Referring to FIG. 17, the fixation point or "fixation location indicator" is a card 253 located in a corner of the display area 121, with two other cards 251 and 252 positioned at the top-left edge and bottom-right edge, respectively, of the display area 121. As before, the player use the finger tap 247 to briefly reveal the faces of the cards 251-253. Referring to FIG. 18, while fixating on the pattern on the face of the card 253, the player notes patterns 251 and 252 in the perifoveal visual field. Referring to FIG. 19, the player chooses between cards 251 and 252 based on the memory of which card held the same pattern as the fixation card 253. And, as with other embodiments, the player also has the choice of a "cannot see" button 258. In this example, the player chose the correct card 252 and is rewarded with a visual symbol 259 (FIG. 20) and the game score 256 is incremented.

Figure 21:
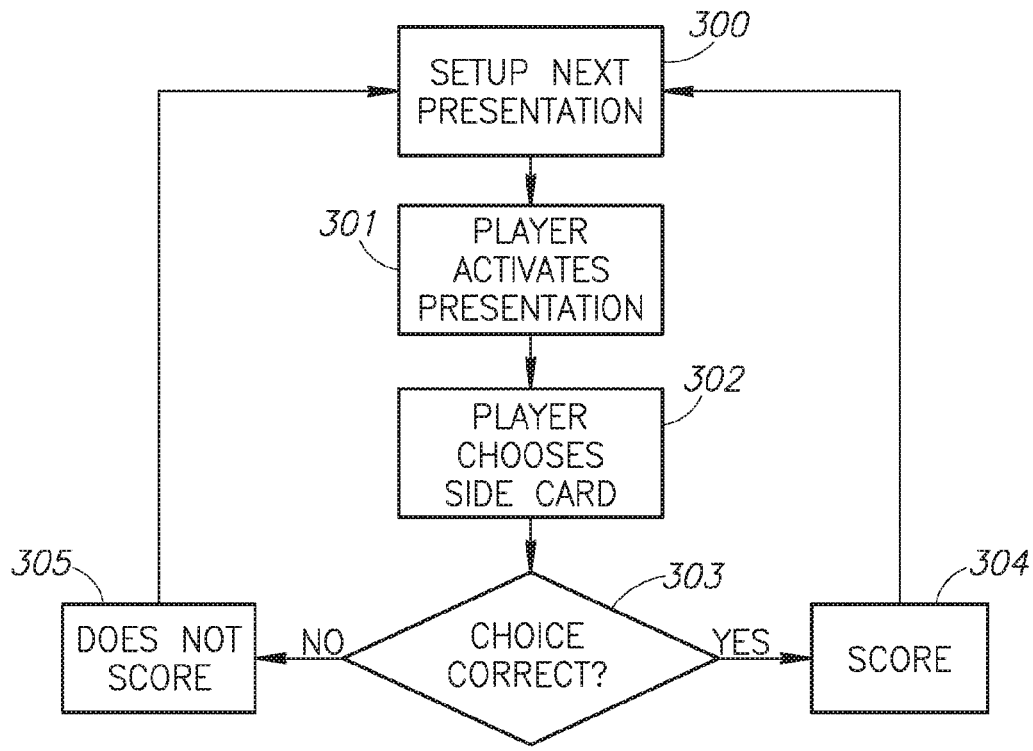
FIG. 21 is a flowchart depicting the logic flow of a cycle of the flash game shown in FIGS. 5-20.

Each round of the flash card game provides one data point on one location in the parafovea or perifovea. The game round can be described by a flow chart (see FIG. 21) for acuity perimetry testing. First, the presentation is set up at 300 by dealing the cards face down. Then, the acuity targets (shifted and aligned line patterns) are presented for a brief moment when the player gives a signal (e.g., a finger tap) to do so at 301. The parafoveal or perifoveal location being tested is the side card with the same line pattern as the central card. The player must choose (e.g., by finger tap) the correct location (or card) at 302. If the choice is correct, decision 303 equals yes, then the score is incremented at 304. If the choice is incorrect, decision 303 equals No, then the score is not incremented at 305. The next round of the game is then played.

Mapping of Stimulus Perception Threshold

One output of the flash game is an acuity perimetry map. The dimension of the map is preferably approximately 16 degrees, which can be easily accommodated by tablet computers currently on the market. For example, the iPad 2® has a display area that is 5.8 inches wide. This provides a maximum visual field width of +/−18 degrees at a viewing distance of 18 inches. With the use of off-center fixation, 16 degrees of testing can be accomplished even on a smart phone screen.

Figure 22:
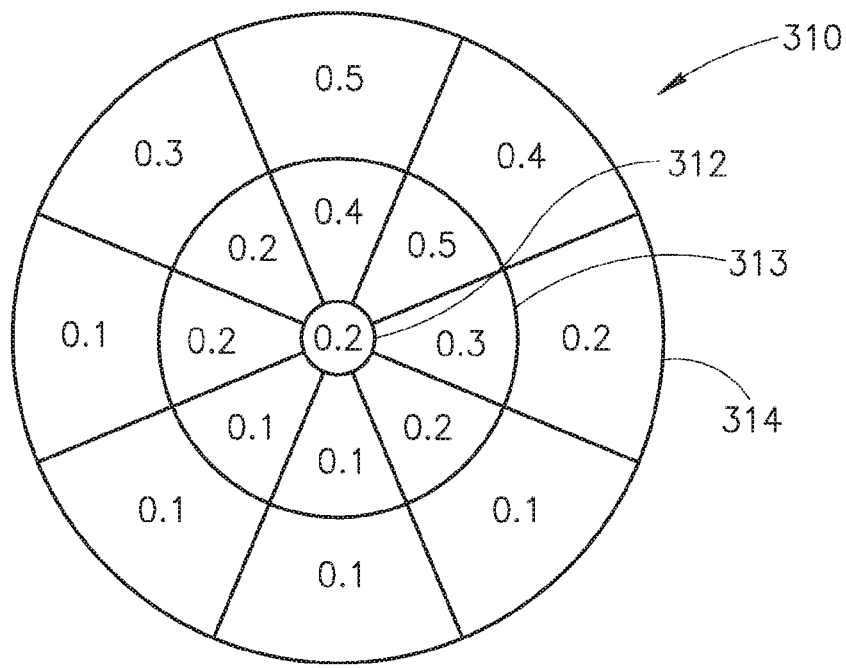
FIG. 22 depicts an exemplary Vernier acuity LogMAR deviation map output from the flash game.

Referring to FIG. 22, an acuity perimetry map 310 is presented as a polar grid of acuity values on the logarithm of minimum angle of resolution (LogMAR) scale. On the LogMAR scale, normal acuity (for the location) has a value of zero. Each ten-fold increase in the size of target needed for threshold perception increases LogMAR by 1.0. A LogMAR of 0.3 indicates that approximately a two-fold increase in target size is needed for threshold perception. Acuity is preferably determined to a precision of 0.1 LogMAR units. For the purpose of AMD screening and monitoring, targets of high contrast are used. The polar grid is divided into a central region 312 spanning the central 3 degrees diameter, parafoveal region 313 spanning the annulus from 3 degrees to 8 degrees diameter, and perifoveal region 314 spanning the annulus from 8 degrees to 16 degrees diameter. The parafoveal and perifoveal annuli are each subdivided into eight sectors. FIG. 22 represents one implementation. More or fewer sectors or annuli could be employed. Rectangular grids could be also be employed instead of a polar grid as well. The map division shown in FIG. 22 may be preferred because the number of test locations (i.e., 17 test locations) is reasonable and the sampling density is appropriately weighed with denser central sampling.

The map 310 is measured over many rounds of the game. The central acuity is tested in the initial rounds of the open card game as described above. The central acuity limits the smallest acuity target that could be used to test parafoveal and perifoveal vision. Then, a series of flash card games are played. The distribution of target locations depends on test location of the number of choices given. For example, a two-choice (two choices of side cards plus one central card=three total cards) game is shown in FIG. 10, where card 233 is the location where acuity is being tested and card 231 is placed in the location opposite the test location, also within the parafoveal annulus. An example of a 4-choice game is shown in FIG. 14, where card 244 is the location of acuity testing and three other cards (241, 242, and 245) are distributed evenly in the perifoveal annulus.

At the beginning of the game, the number of tests at each location can be found in column 2 of Table 1 shown above. For example, for a two-choice game, five tests are needed at each location. Since there are 16 parafoveal and perifoveal test locations (see FIG. 22), a total of 80 flash card rounds are needed. These rounds are randomly ordered into a game sequence and played. At each round, the central target line pattern is randomly assigned to be either aligned or shifted. After the primary flash card rounds, the acuity target at a location is considered to be perceived if it is correctly chosen in all tests (e.g., five out of five times for the two-choice game), and considered not perceived if two or more incorrect choices are made. The test results at some locations could be equivocal (e.g., one error out of five choices), and three more tests are needed at these locations. These secondary flash card rounds are also randomly sequenced and played. After the secondary flash card rounds at each location, the target is considered perceived if only one or less incorrect choice is made, and is considered not perceived if two or more incorrect choices are made. Depending on perception, the target size at each location is then incremented or decremented for the next series of flash card rounds. The game series are played until enough information is accumulated to determine the LogMAR acuity map.

Figure 23:
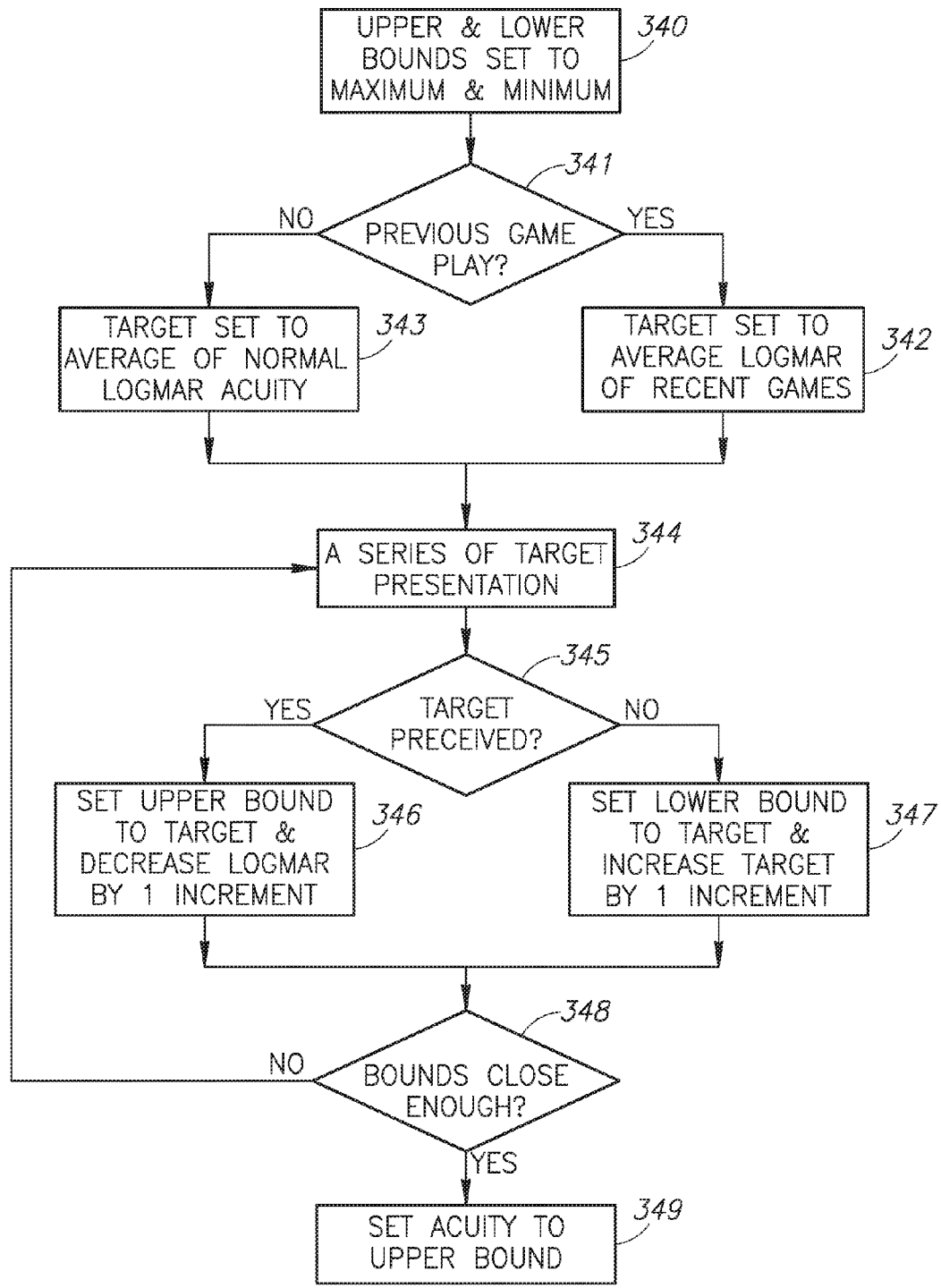
FIG. 23 is a flow chart depicting the testing cycle used to establish the acuity at one visual location.

The series of testing needed to determine LogMAR is determined by an iterative bracketing algorithm. Referring to FIG. 23, the upper and lower bounds of LogMAR acuity at a parafoveal or perifoveal location are initially set to the largest and smallest possible targets at 340. The initial size of the acuity target is set according to a best guess. If the game has been played before, decision 341 equals yes, then the best guess may be the average of recent games at 342.

For example, the results of the most recent three games in the past month could be averaged. If no game had been played before, decision 341 equals No, the best guess may be the average LogMAR acuity level at the same test location for a normal reference population.

The target is then presented in a series of flash card games as described above at 344. If the target is perceived, decision 345 equals yes, then the LogMAR upper bound is set to the target size and the target size for the next series of flash card tests is set one increment smaller at 346. The increment of target sizing is preferably 0.1 LogMAR units. If the target is not perceived, decision 345 equals No), then the LogMAR lower bound is set to the target size and the target size for the next series of testing is made one increment larger. If the upper and lower bounds are more than 0.1 LogMAR unit apart, decision 348 equals No, then additional series of game testing are done at the test location at 344 using the new target size. If the upper and lower bounds are only 0.1 LogMAR unit apart or less, decision 348 equals Yes, then no more testing is necessary at the location and the acuity output at the location is set to the upper bound (smallest target shown to be perceived) at 349. Other methods for approaching and determining the threshold value may be used. For example, rather than incrementing or decrementing the target size by 1 increment each interval, the target size may be set half way between the upper bound and lower bound at each interval.

The number of choices in each flash card round should be determined by the ability of the player to rapidly process visual information. This ability will increase as more games are played. Thus, preferably, a two-choice flash card game is played initially, and then the player is given the opportunity to advance to a three-choice game if the score is high. Following this, the player is again given the opportunity to advance to a four-choice game if the score is high. Higher number of choices at each round means fewer rounds are needed (see Table 1 above). This leads to a shorter and more challenging game. However, because the primary purpose of the game is to test retinal function rather than visual processing, the number of choices per round is preferably kept relatively low (e.g., between two and four choices) so mistakes due to inattention are infrequent.

Alternative Test Targets

Figure 24:
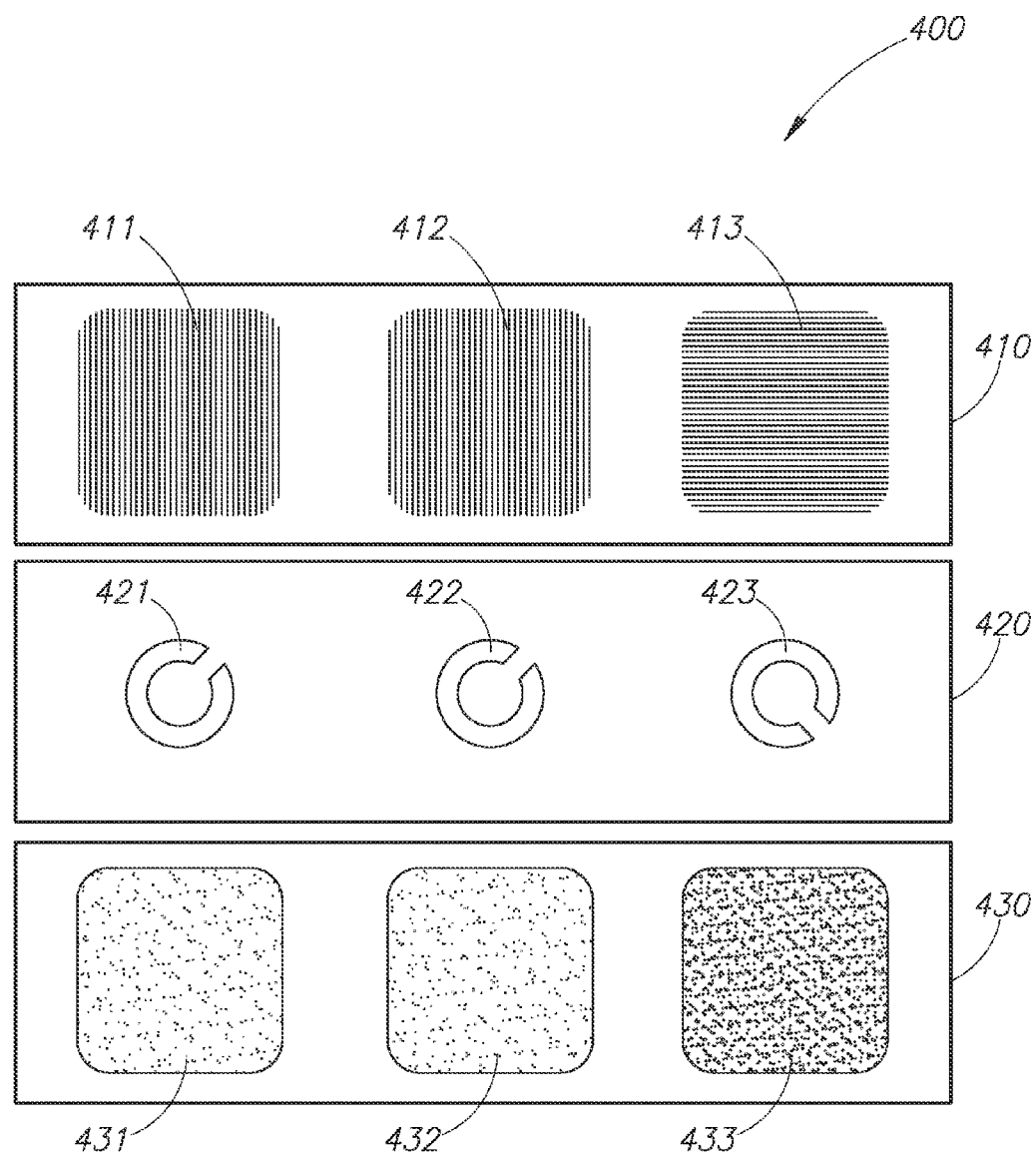
FIG. 24 illustrates alternative resolution acuity testing targets and gray-scale testing targets.

The tests so far illustrated utilized Vernier acuity targets. But it should be appreciated that alternative targets could be used to test different aspects of vision. For example, referring to FIG. 24, the targets could test line orientation 410 (targets 411, 412, and 413), Landolt C orientation 420 (targets 421, 422, and 423), color or gray level 430 (targets 431, 432, and 433 having differing gray levels or color levels), color value or saturation (not shown), commonly used Snellen letter or tumbling E acuity targets (not shown), or other targets could be used.

Advantages

Embodiments of the present invention comprise a video game-based acuity perimetry test that has some or all of the following advantages as well as other advantages:
1) Embodiments of the present invention can be implemented on common consumer-owned hardware platforms such as a smart phone, laptop computer or a tablet computer (e.g., an iPad 2®). This allows more frequent testing by users.
2) The central fixation point is established by forcing the player to know the pattern of the central card. Thus, there is less chance of error due to the player cheating or otherwise shifting central gaze to a peripheral target.
3) For smaller screens, the fixation point is placed off-center to allow testing of perifoveal vision.
4) The video game uses interesting visual stimuli, visual action, and background scenery to help hold a user's attention.
5) The video game uses background music and action-generated sounds to help hold the user's attention.
6) The video game keeps a score related to a user's performance towards goals to help hold the user's attention and motivate repeated playing of the game.
7) The pace of the game is controlled by the player.
8) The distance between the eye being tested and the display screen is established by video imaging of the occluder, obviating the use of a chin rest or other devices to fix the head position relative to the display screen.
9) The ambient light level is monitored by the video camera included in the apparatus of the current invention.

Thus, the present invention provides a "home test" that can be self-administered by subjects who have AMD or are at risk for AMD, so that the test can be performed frequently (e.g., daily or weekly, etc.). The test may be in the form of a game that can maintain player interest. And the resulting macular acuity map may be automatically analyzed by a computer and transmitted electronically to a physician or healthcare provider who monitors the patient's eye health.

Example Hardware Environment

Figure 25:
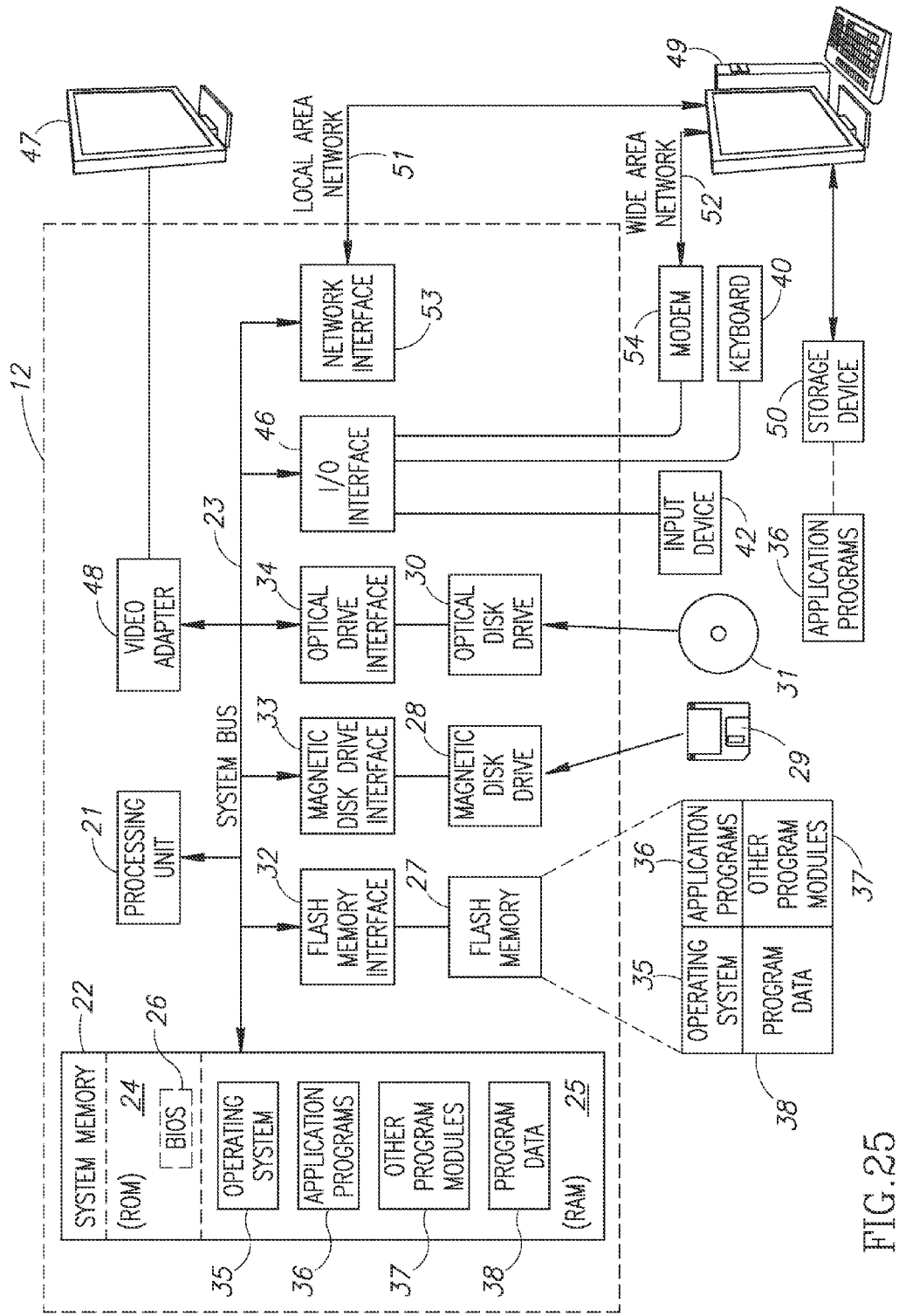
FIG. 25 is a diagram of a hardware environment and an operating environment in which the computing devices of the systems disclosed herein may be implemented.

FIG. 25 is a diagram of hardware and an operating environment in conjunction with which implementations of the device 100 may be practiced. The description of FIG. 25 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types. The program modules may be stored and distributed via networks or the internet, by way of non-limiting example.

Moreover, those skilled in the art will appreciate that implementations may be practiced with other computer system configurations, including hand-held devices, multi-processor systems, microprocessor-based or programmable consumer electronics, network PCs, minicomputers, mainframe computers, tablet computers, smartphones, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 25 includes a general-purpose computing device in the form of a computing device 12. The device 100 may be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like. The computing device 12 may be a tablet computer, a smart phone, a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a flash memory 27, a magnetic disk drive 28 for reading from or writing to a removable magnetic disk 29, and an optical disk drive 30 for reading from or writing to a removable optical disk 31 such as a CD ROM, DVD, or other optical media.

The flash memory 27, magnetic disk drive 28, and optical disk drive 30 are connected to the system bus 23 by a flash memory interface 32, a magnetic disk drive interface 33, and an optical disk drive interface 34, respectively. The drives and their associated computer-readable media provide non-volatile storage of computer-readable instructions, data structures, program modules, and other data for the computing device 12. It should be appreciated by those skilled in the art that any type of computer-readable media which can store data that is accessible by a computer, such as magnetic cassettes, hard disk drives, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the flash memory 27 and other forms of computer-readable media (e.g., the removable magnetic disk 29, the removable optical disk 31, flash memory cards, hard disk drives, SSD, USB drives, and the like) accessible by the processing unit 21 may be considered components of the system memory 22.

A number of program modules may be stored on the flash memory 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and input device 42. The input device 42 may include touch sensitive devices (e.g., a stylus, touch pad, touch screen, or the like), a microphone, joystick, game pad, satellite dish, scanner, video camera, depth camera, or the like. In a preferred embodiment, the user enters information into the computing device using an input device 42 that comprises a touch screen, such as touch screens commonly found on tablet computers (e.g., an iPad® 2). These and other input devices are often connected to the processing unit 21 through an input/output (I/O) interface 46 that is coupled to the system bus 23, but may be connected by other types of interfaces, including a serial port, parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feedback game controller).

The computing device 12 may operate in a networked environment using logical connections (wired and/or wireless) to one or more remote computers, such as remote computer 49. These logical connections are achieved by a communication device coupled to or a part of the computing device 12 (as the local computer). Implementations are not limited to a particular type of communications device or interface.

The remote computer 49 may be another computer, a server, a router, a network PC, a client, a memory storage device, a peer device or other common network node or device, and typically includes some or all of the elements described above relative to the computing device 12. The remote computer 49 may be connected to a memory storage device 50. The logical connections depicted in FIG. 25 include a local-area network (LAN) 51 (wired or wireless) and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network (e.g., a mobile communications network such as 3G, 4G, etc.), or power lines. Such a modem may be connected to the computing device 12 by a network interface (e.g., a serial or other type of port). Further, many laptop or tablet computers may connect to a network via a cellular data modem.

When used in a LAN-networking environment, the computing device 12 may be connected to the local area network 51 through a network interface or adapter 53 (wired or wireless), which is one type of communications device. When used in a WAN networking environment, the computing device 12 typically includes a modem 54, a type of communications device, or any other type of communications device for establishing communications over the wide area network 52 (e.g., the Internet), such as one or more devices for implementing wireless radio technologies (e.g., GSM, etc.).

The modem 54, which may be internal or external, is connected to the system bus 23 via the I/O interface 46. The modem 54 may be configured to implement a wireless communications technology (e.g., mobile telecommunications system, etc.). In a networked environment, program modules depicted relative to the personal computing device 12, or portions thereof, may be stored in the remote computer 49 and/or the remote memory storage device 50. It is appreciated that the network connections shown are exemplary and other means of and communications devices or interfaces for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

Second Embodiment

A second embodiment of the present invention is directed to a video game to map a test subject's peripheral vision. In some embodiments, the video game comprises a moving visual fixation point that is actively confirmed by an action performed by the test subject and a test for the subject to locate a briefly presented visual stimulus (e.g., 0.1 seconds, 1 second, etc.). The game is implemented on a hardware platform comprising a video display, a user input device, and a video camera. The camera is used to monitor ambient light level and the distance between the video display and the eyes of the test subject. The game serves as a visual field test that produces a map of the thresholds of visual perception of the subject's eye that may be compared with age-stratified normative data. The test is suitable to be administered by the subject (also referred to as player or user herein) with or without professional supervision. The results may be transmitted to a health care professional or other entities by telecommunications means to facilitate the diagnosis and/or monitoring of glaucoma or other relevant eye diseases.

The physical apparatus of the current invention (the device) include a computer with a video monitor, a video camera, and a human user input device. An integrated apparatus serving these functions is the iPad2 (Apple Inc., Cupertino, Calif.) and other tablet computers with similar functionalities. Alternatively, many smartphone also possess the same functionalaities and could be used as the device platform.

Figure 26:
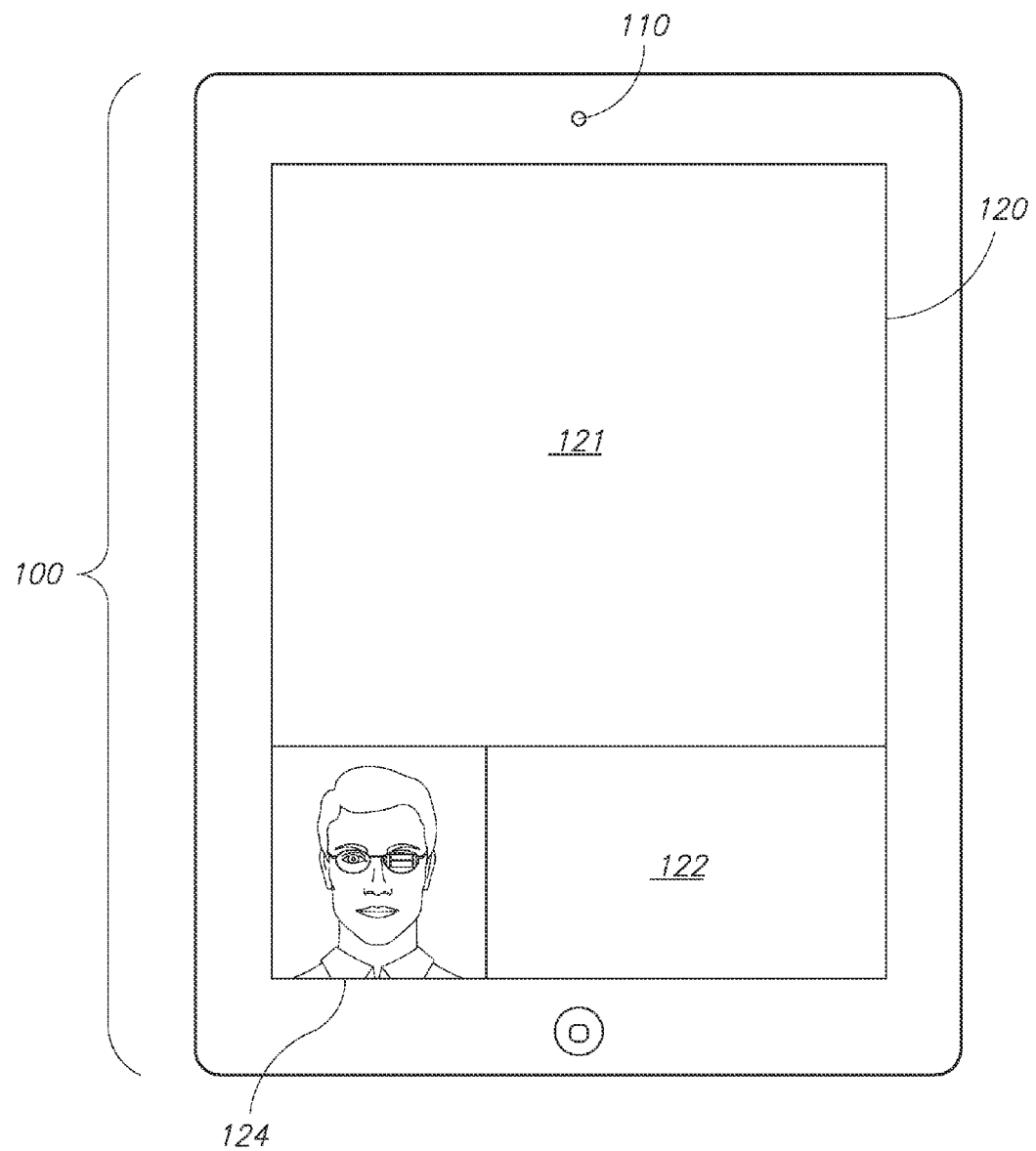
FIG. 26 illustrates a display, input device, and distance-monitoring camera features of a second embodiment of the invention implemented using a tablet computer.

Referring to FIG. 26, the device 100 has the video camera 110 to monitor the distance between the device and the test subject's eyes and also to monitor the ambient light level. The touch screen video display 120 is divided into main game play area 121, ancillary area 122, and eye monitor area 124. Play area 121 is used to display the visual action of the game. The play area is preferably approximately square. The ancillary area 122 is used as the ancillary human user input and score display. Eye monitor area 124 is used to display the image captured by the video camera 110 for help with aiming the camera. The device 100 may rest on a stand 145, as previously discussed with reference to FIG. 2.

As previously discussed with reference to FIGS. 3A-3C, the occluder 160 is used to occlude vision in one eye so the other eye could be tested using the video game of the current invention. The eyes are tested in a sequential fashion. One eye is tested while the other eye is occluded. The occluder 160 could be mounted on spectacles 150 or be fixed on the user's head using straps. The occluder 160 has visual feature 165 of known dimensions which is captured by video camera 110 and analyzed by the computer to monitor the distance between the subject's eyes and the device 100. The visual feature 165 could be for example a horizontal bar 165A with well-defined terminations (e.g., vertical bars 165B and 165C) so that the length of the bar could be easily determined by computerized automatic image processing. Other shapes or patterns, such as a circle or rectangle, could also be used. Based on the video analysis, the device 100 may display an instruction 140 on the video display 120 (and/or by sound) so the user can position his or her head within the optimal range of distance from the device, as previously discussed.

An alternative method of obtaining the desired viewing distance D asks the user to adjust the viewing distance until the size of the real-time video display the occluder 160 has the correct size, as previously discussed with reference to FIG. 3C. A further alternative method for the device to monitor viewing distance is to analyze the size of the eye (corneal width from limbus to limbus) being tested or other features on the subject's face. For this alternative to work a video frame must first be taken when the face is at a known distance from the camera 110. The distance could first be established using a measuring tape or ruler with known length.

Referring back to FIG. 4, the input device 123 and the output device 120 are connected to the computer 166 of the device 100. The term computer here refers to the central processor, memory, and data bus as opposed to the peripheral input and output devices. The input and output functions can both be performed on the same touch screen, as depicted in FIG. 26. The video camera 110 produces image frames that are processed by computer 166 to monitor the distance between the subject's eyes to the device 100 and to assess ambient light level. The subject produces action in the video game with the input device 123 and the game background and actions are displayed on the video display or output device 120. The game sounds are output on the speaker 125. The real-time image of the subject's face (most importantly to include the occluder 160 and test eye) is displayed on eye monitor area 124. The subject produce action in the game with input device 123 and the game background and actions are displayed on video display 120. The game sounds are output on speaker 125.

The test results may be transmitted or uploaded (e.g., wirelessly) to the server 168 over the network 167 (e.g., the Internet, a mobile communications network, etc.). This feature allows for the storage, tracking, review, and analysis of the test results over time to detect patterns, such as the deterioration of a patient's vision. The patient, his or her healthcare professionals, or others may access the data stored on the server 168 through a web browser or via a link to an electronic health record system of a healthcare facility. The test results data may be processed and presented in a manner that is useful for the patient and/or healthcare provider to analyze the results.

The server 168 may also be configured to provide notifications or alerts to the patient or their healthcare provider for any changes in vision that may require further attention or treatment. These alerts may be sent to a patient's and/or healthcare provider's electronic devices (e.g., the mobile phone 169) via email, SMS messages, voice messages, or any other suitable messaging system. For example, if an analysis of the uploaded test results reveals that a patient's vision is deteriorating, the server 168 may automatically send a message to the patient and/or a healthcare provider to alert them of the change in condition. Thus, appropriate action or treatment may be provided.

Initial Setup

The user is instructed to perform the setup steps by the device without need of human professional instruction and supervision. Though a human supervisor could be helpful to assure proper use.

The first time the subject is taking the test, the subject's identifying information is entered into the computer. Information is also entered to allow transmission of the test results to a physician who is monitoring the subject's eye health with regard to AMD or other macular diseases.

Since the game is used to perform a preferential hyperacuity perimetry test, the terms "game" and "test" are used interchangeably in this application. The user of the device is the subject of the MAP test and the game player. Therefore the terms "user," "subject," and "player" are also used interchangeably.

Before each game, the ambient light is adjusted to the desired range by the use of camera 110. If the light detected by the camera is too high or low, a message is displayed on display area 120 directing the user to appropriately adjust the light level for proper administration of the test. The test is administered with light level in the low scotopic range. The brightness and contrast of the display is preferably set at a standard. Alternatively, the display brightness can be varied to compensate for background light level if the background cannot be brought into standard range.

The test is administered at a viewing distance that is sufficient to provide useful AMD diagnostic information. For example, the iPad2 has a display area that is 5.8 inches wide. Referring back to FIG. 26, the display area 120 uses this full width. This provides a maximum perimetry testing area of 18 degrees full width at a viewing distance of 18 inches, using the methods of the current invention. The device 100 monitors the viewing distance by taking images of the user's face (see FIGS. 3A & 3C) with camera 110 (see FIG. 26). The computer analyzes the visible feature 165 on the occluder 160 to compute the distance between the camera 110 and the occluder 160, which is approximately the same as the viewing distance. At the setup of each game, the device 100 instructs the user to move his (or her) head into position so the image of the face (in particular the occluder 160) may be captured by camera 110 and displayed in the eye monitor area 124. It then instructs the user to move closer to or farther from the display area 120 to bring the user's eyes into the target range of viewing distance of the device 100. The initial target range may be 17-19 inches for example. During the game, the device 100 continues to monitor the viewing distance and provides a warning and instruction for the user to move closer to the display area 120 if the user is out of range. The operating range may be 16-20 inches for example. The user should be wearing spectacle correction for best vision within the operating range of the viewing distance. For an emmetrope, a pair of reading glasses with power of +2.25 D would be optimal for the viewing distance of 18 inches. If spectacles are used, the occluder 160 should be mounted over the spectacle lens over the eye not being tested. If no spectacles are needed or if the subject is using contact lenses, the occluder 160 could be mounted over plano glasses or strapped on as an eye patch.

Game Playing and Preferential Hyperacuity Perimetry Test Cycle

Figure 27:
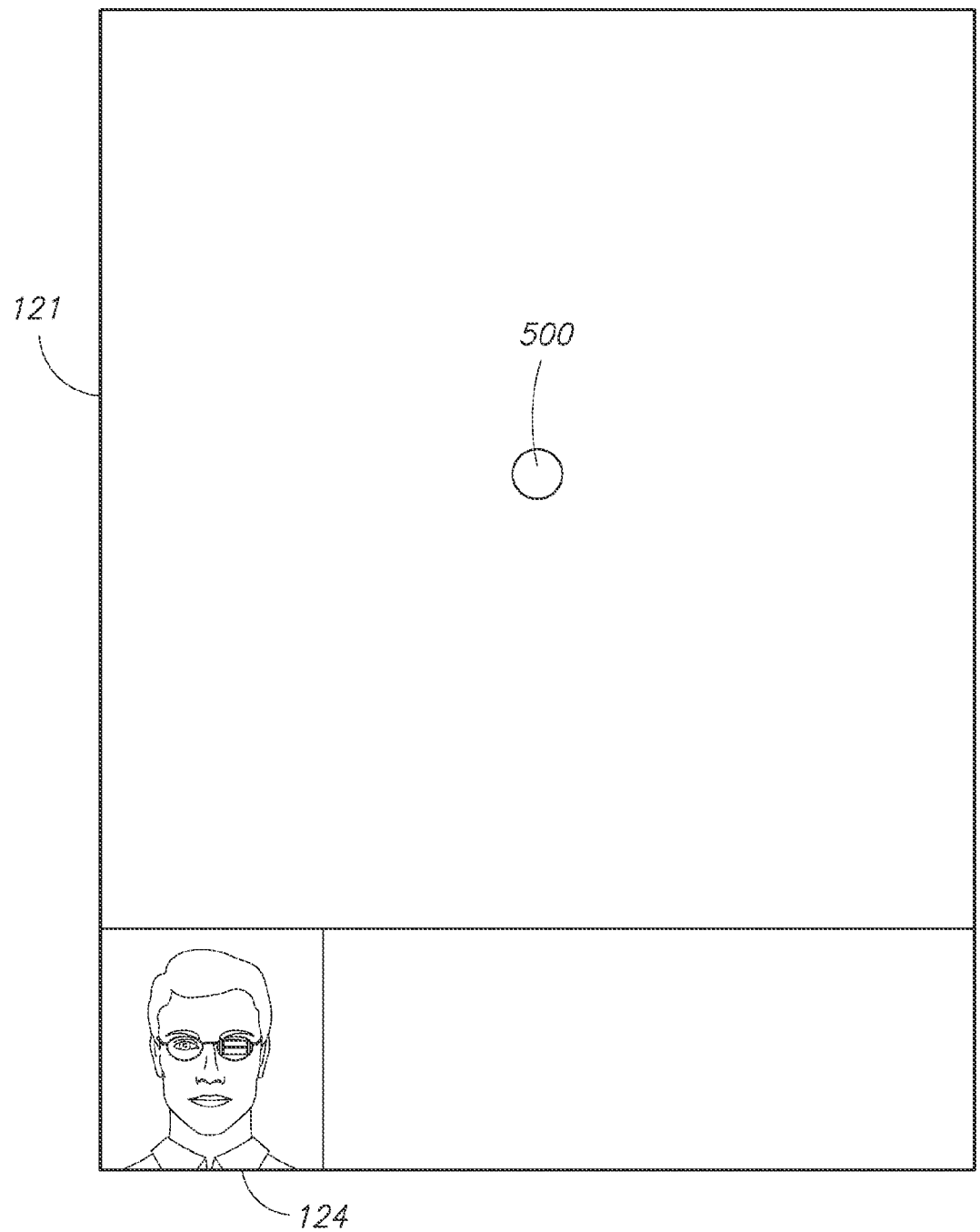
FIG. 27 illustrates a first screen shot of a musical wheel game measuring central acuity in accordance with an embodiment.

Referring to FIG. 27, a central fixation dot or target 500 is projected on the play area 121 of the device 100. The player is instructed to fix his (or her) gaze on the central fixation target 500. The player's face is captured and displayed in eye monitor area 124 for the purpose of monitoring the distance between the player's eyes and the device, which can be hidden in order not to distract players from the test (location and distance of the player's eyes are still monitored and appropriate warnings will be given even when the player's face is hidden on the video display 120).

Figure 28:
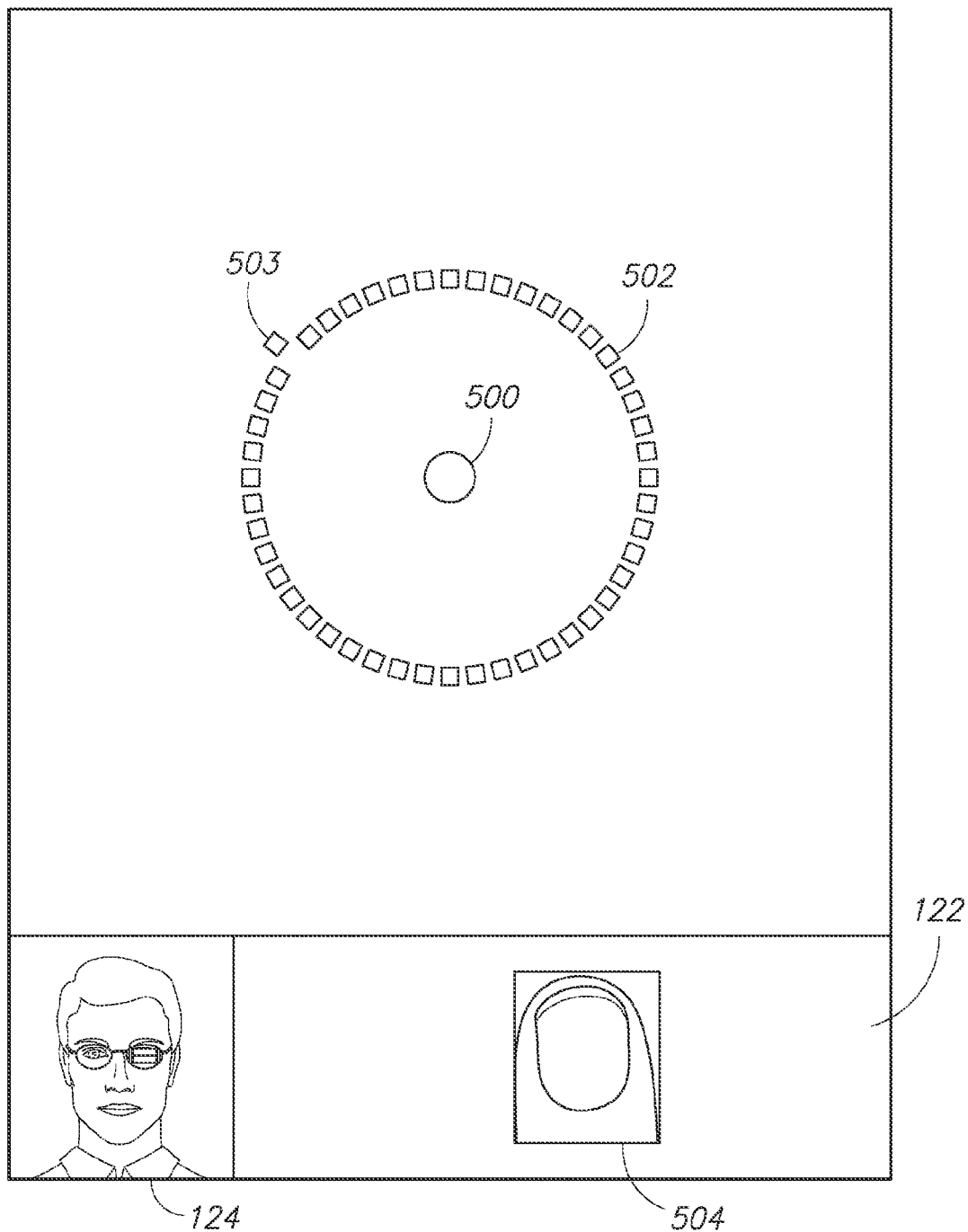
FIG. 28 illustrates a second screen shot of a musical wheel game measuring central acuity in accordance with an embodiment.

Referring to FIG. 28, the player makes sure his gaze is fixed on the central fixation target 500 and then activates flash presentation of a hyperacuity target 502 by a finger tap 504 on the ancillary area 122. A circular hyperacuity target 502 is a circle of dots with a focal distortion 503. The circular target 502 is centered on the central fixation target 500. The circle preferably has 3 possible diameters matching the 3 macular areas being tested: fovea, parafovea and perifovea. The fovea spans approximately a 1 mm (3° visual angle) diameter area, and a circle of 2° visual angle (diameter) would be appropriate for testing foveal vision. The parafovea spans approximately the 1-2.5 mm (3-8° visual angle) diameter annular area, and a circle of 6° diameter would be appropriate for testing parafoveal vision. The perifovea spans approximately the 2.5-5.5 mm (8-18° visual angle) diameter annular area, and a circle of 12° visual angle (diameter) would be appropriate for testing perifoveal vision. FIGS. 27-31 show an example where parafoveal vision is tested. The target 502 is presented for a fraction of a second (for example 0.2 second). The contrast between the target and background is preferably high. There is a distortion 503 where a dot deviates from the other dots forming the circle. In this example the distortion is in the upper left sector. The player was instructed to maintain gaze fixation on target 502 while noticing in which sector the largest distortion is located. The distortion in the regular circular pattern represents a vernier or "hyperacuity" distortion target. Identifying the location of the distortion is a preferential hyperacuity task. The magnitude of the distortion is preferably large enough to be detected by 7 out of 8 times on the average by a normal population. Larger distortion could be used to provide larger probability of detection by a normal human eye.

Figure 29:
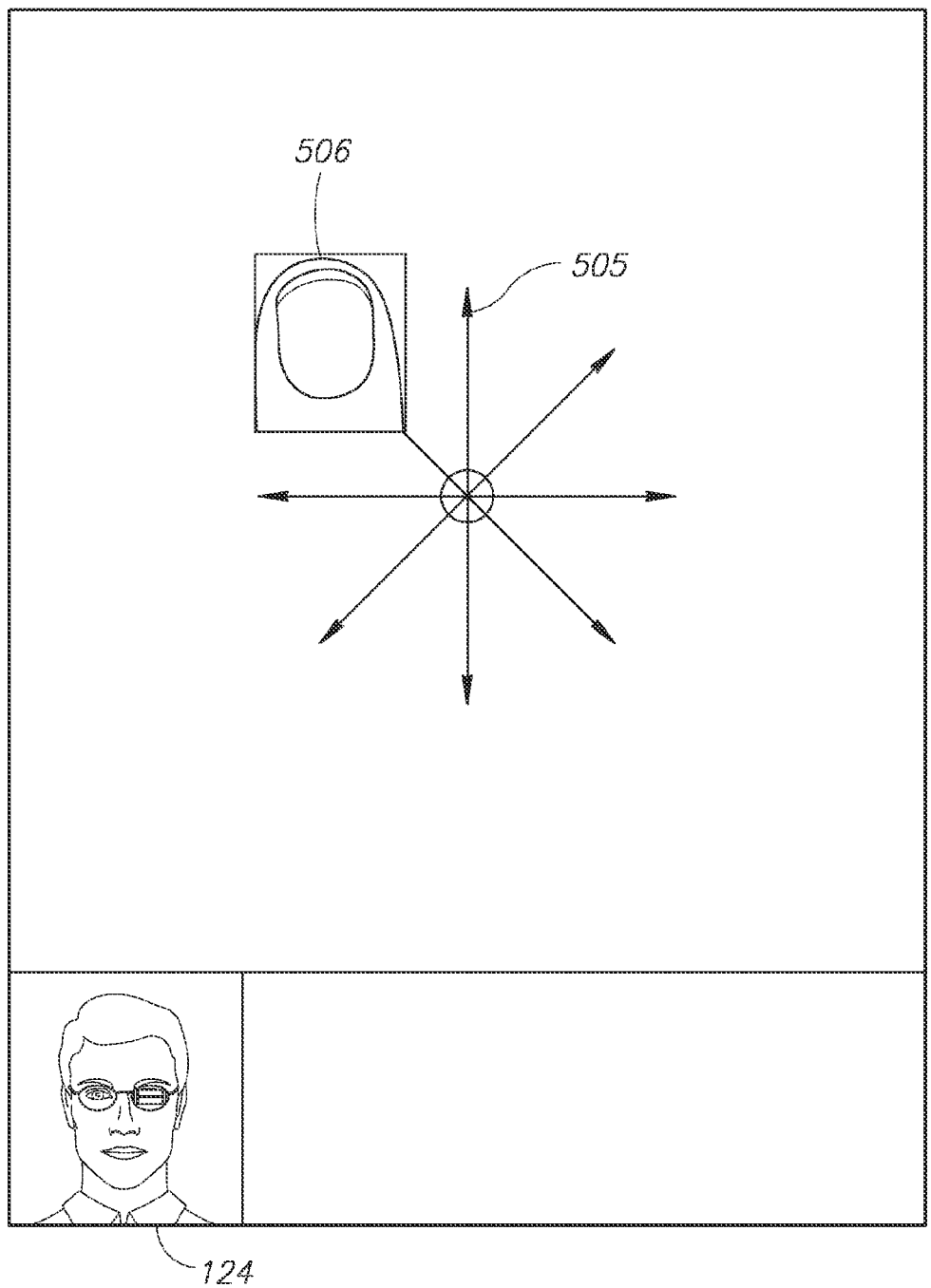
FIG. 29 illustrates a third screen shot of a musical wheel game measuring central acuity in accordance with an embodiment.

Referring to FIG. 29, the choice screen display is then presented on the play area 121. It shows a set of 8 arrows 505 pointing to the 8 angular sectors (directions) being tested. The distortion 503 was presented in one of the 8 sectors. The player places a finger tap 506 in the sector of greatest perceived distortion. In this example, the player uses finger tap 506 to indicate that he saw the distortion in the top left sector. This correct choice of sector suggests that the subject was able to see the projected distortion. On the other hand, if the player chooses an incorrect sector (see FIG. 30) by placing finger tap 506 on the bottom arrow, then either he was unable to see the distortion 503 (scotoma at the location of the projected distortion) or a macular pathology produced a greater perceived distortion (metamorphopsia at the location of the perceived distortion) than the projected distortion.

Of course, a single round of test cannot establish scotoma or metamorphopsia at a given location, a number of rounds are needed. The probability of a scotoma or metamorphopsia can be calculated using Equation 2.

$$P_C(x) = \frac{n!\left(\frac{1}{c}\right)^x \left(1-\frac{1}{c}\right)^{n-x}}{x!(n-x)!} \qquad \text{Equation 2}$$

where
$P_C(x)$ is the probability of the number of same choices being arrived at by random chance,
x is the number of rounds in which the same choice was picked,
n is the total number of rounds played,
1/c is the probability of the choice in each round, Using Equation 2, the probability to arriving at the same choices by random chance is tabulated for 4 to 7 rounds of the game (Table 2). In this example, we simplify the calculation by assuming that the chance of not choosing the correct sector with the distortion 503 by a normal person is ⅛, the same as the number of sectors. So for both scotoma (relative to normal vision) and metamorphopsia calculations, c=8. Table 2 shows that playing 5 rounds of games at each test location is reasonable game design. In 5 rounds, if the player chooses the wrong sector (where the distortion 503 was NOT projected) 2 times, one can be approximately 90% sure that a scotoma exists. If the player chooses the wrong sector 3 times, one can be more than 98% sure that a scotoma exists. If the player chooses the wrong sector 4 times, one can be about 99.9% sure that a scotoma exists. If the player consistently chooses a wrong sector and this sector is in the same location (since there are 8 sectors to choose from the chance is ⅛ each round) 4 times in 4 to 7 rounds, then one can be sure that metamorphopsia exists in that location with a probability >99% ($P_C$<1%). Given 3 circle diameters, 8 sectors per circle, and 5 game rounds per location, the minimum number of rounds per game is 120. The 120 rounds are preferably randomly sequenced to avoid boredom. Since each game round only take a few seconds, the entire AMD screening test can be completed in a few minutes. More rounds are needed if metamorphopsia is detected as explained below.

TABLE 2

The number of choices of the same kind needed to establish a metamorphopsia or scotoma at 5 and 1 percentile error levels. A probability of 1/8 for each choice is assumed.

| # rounds | # of same choices | |
|---|---|---|
| | $P_C$ < 5% | $P_C$ < 1% |
| 4 | 2 | 3 |
| 5 | 3 | 4 |
| 6 | 3 | 4 |
| 7 | 3 | 4 |

$P_C$ is the event occurring by random chance (see Equation 1).

Figure 31:
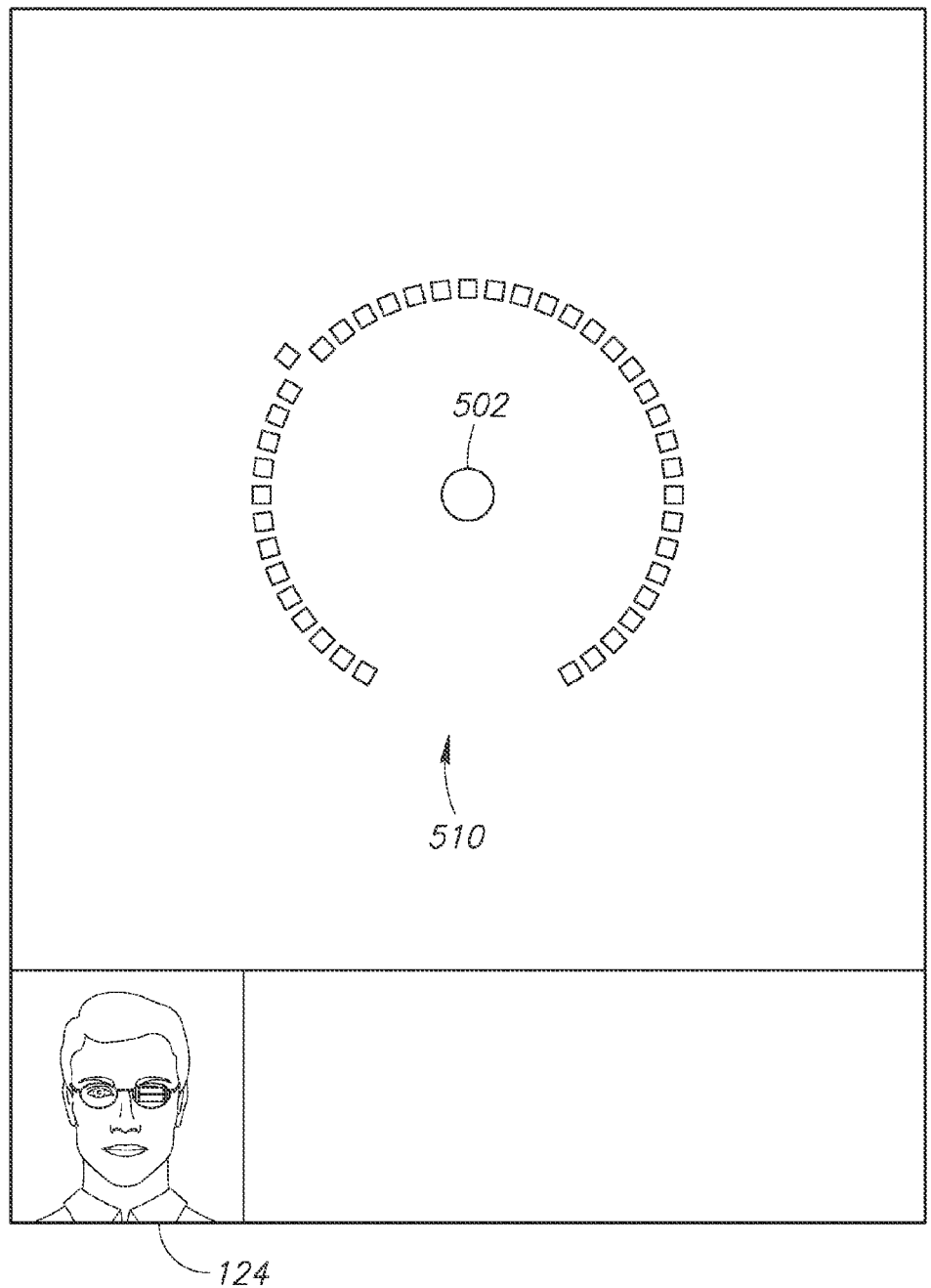
FIG. 31 illustrates a fifth screen shot of a musical wheel game measuring central acuity in accordance with an embodiment.

A dominant metamorphopsia can interfere with the detection of other areas of metamorphopsia or scotoma. Therefore when metamorphopsia is proven at a location with >99% certainty, that location is blocked out in future game rounds. Referring to FIG. 31, a block 510 is placed over the bottom sector location where metamorphopsia was located so the metamorphopsia can no longer be perceived. The arrow 505 to that sector location where metamorphopsia was located, as illustrated in FIG. 29, is also removed to disable that choice. The blocking is done separate for each of the 3 circle diameters: foveal, parafoveal, and perifoveal. After each new block is placed, the game for that wheel is reset to allow accurate scotoma and metamorphopsia detection in the remaining unblocked sectors.

Although the description above employs a distortion in a circle of dots as the hyperacuity target 502 the subject is asked to detect, other circular targets could be used. For example, the circle could be a continuously line and discrete or continuous distortion could be employed as the hyperacuity target. In another implementation, a gap in a continuous circle could serve as an ordinary acuity (not hyperacuity) target. In yet another implementation, a polygonal (e.g. octagon) is used and a missing side is the acuity feature the subject is asked to detect. A significant feature of the current invention is that the acuity or hyperacuity feature is presented on a symmetric target so that the target presentation does not cause the subject's gaze to deviate from the center.

Alternative Target Presentation Scheme

Figure 32:
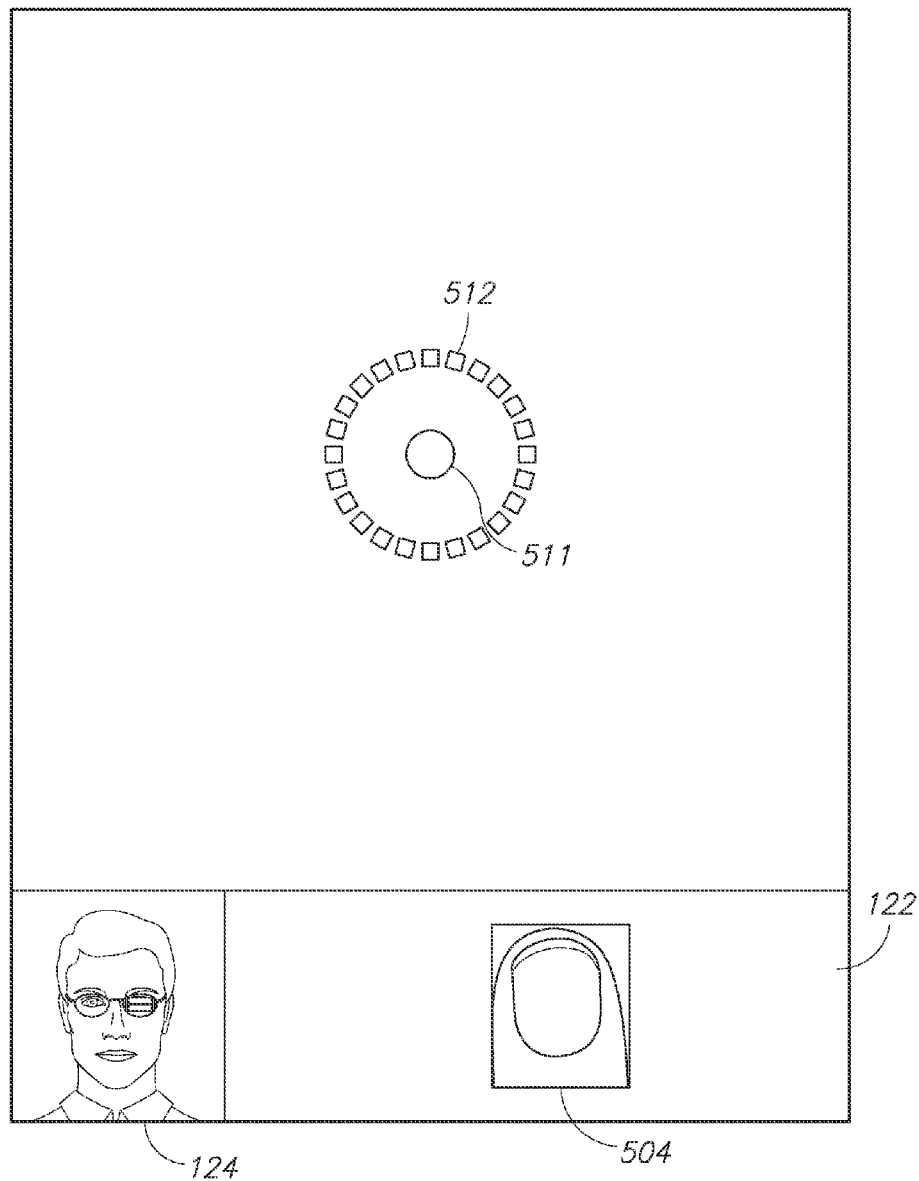
FIG. 32 illustrates a sixth screen shot of a musical wheel game measuring central acuity in accordance with an embodiment.
Figure 33:
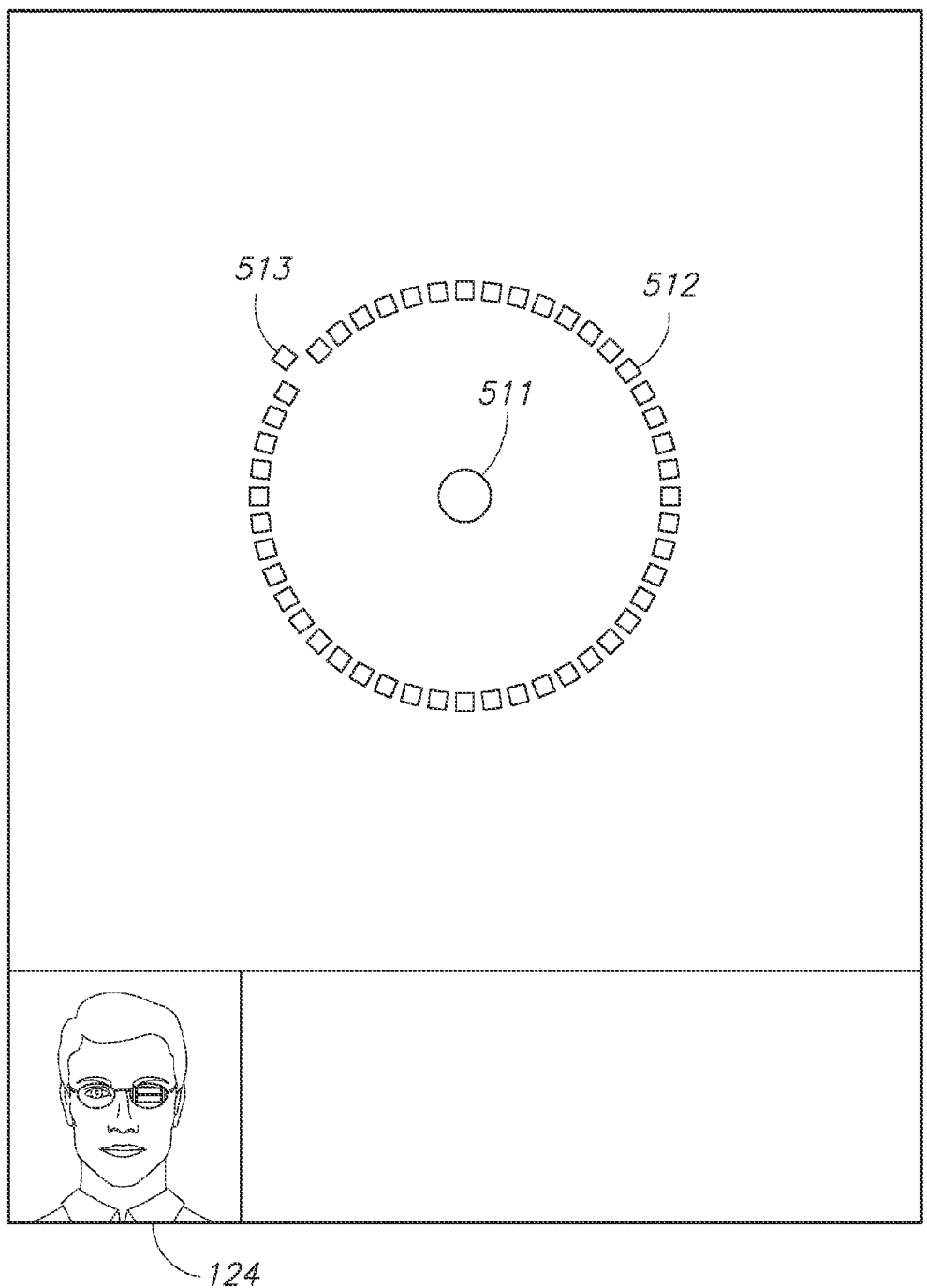
FIG. 33 illustrates a seventh screen shot of a musical wheel game measuring central acuity in accordance with an embodiment.
Figure 34:
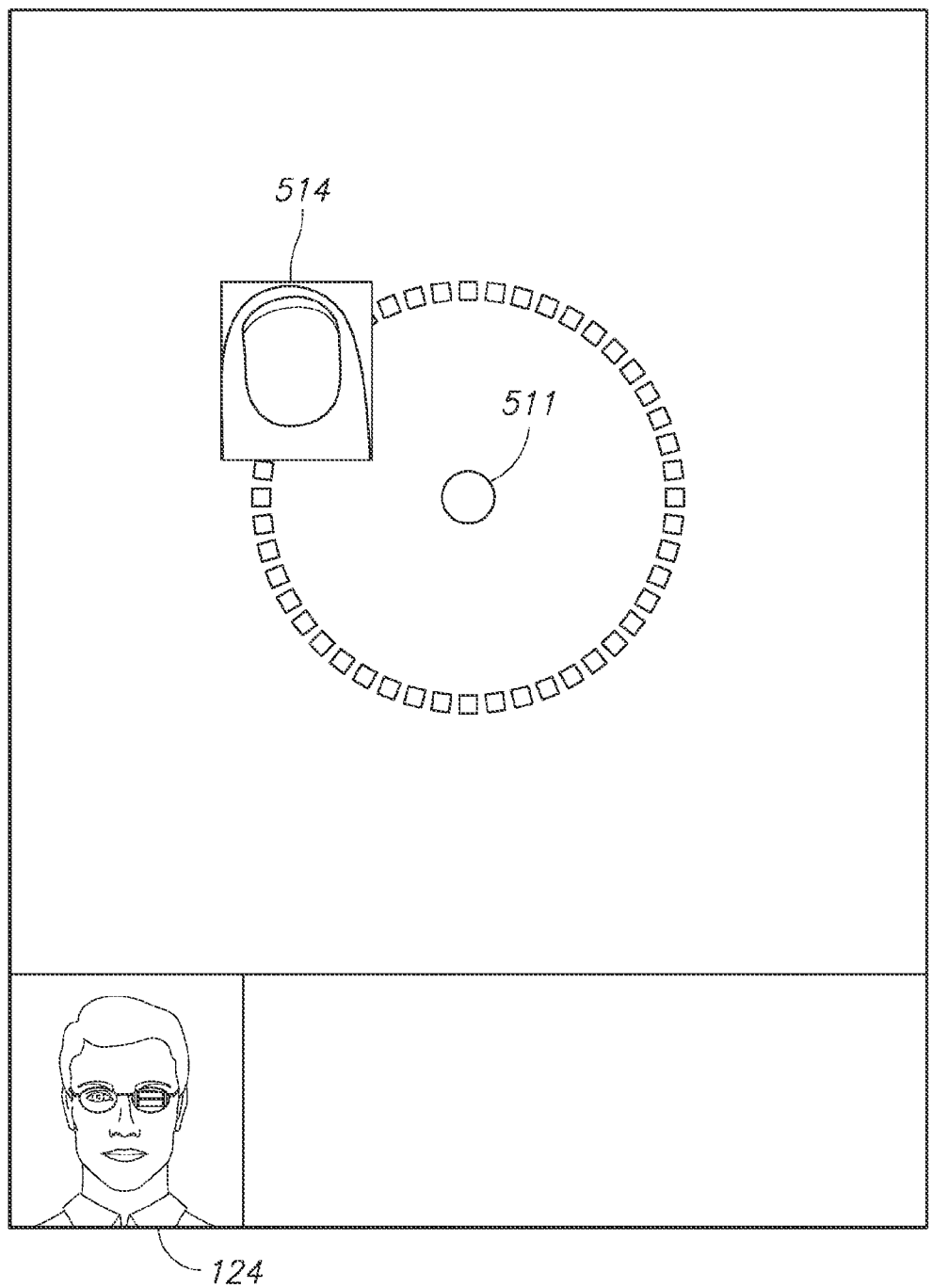
FIG. 34 illustrates an eighth screen shot of a musical wheel game measuring central acuity in accordance with an embodiment.

Since the hyperacuity target 502 is a circle around the central fixation target 500, its presentation does not distract the subject's gaze. Therefore one can employ a smoothly expanding circular target. Referring to FIG. 32, the test cycle starts with finger tap 504. A circular hyperacuity target 512 is initially small, and continuous without any distortion break. Again, it is centered on a central fixation dot or target 511. The circle target 512 expands, as shown in FIG. 33. The subject is asked to tap directly on a break or distortion 513 in the expanded circle target 512 of FIG. 33. Referring to FIG. 34, if the tap 514 is in the correct octant occupied by distortion 513, then it suggests that the hyperacuity distortion target (distortion 513) was successfully perceived by the subject. If the subject fails to tap within a time limit then the distortion was not perceived. If the user taps prematurely or on the wrong octant then a metamorphopsia is likely. These findings are confirmed by repeated rounds of testing as described above.

Figure 30:
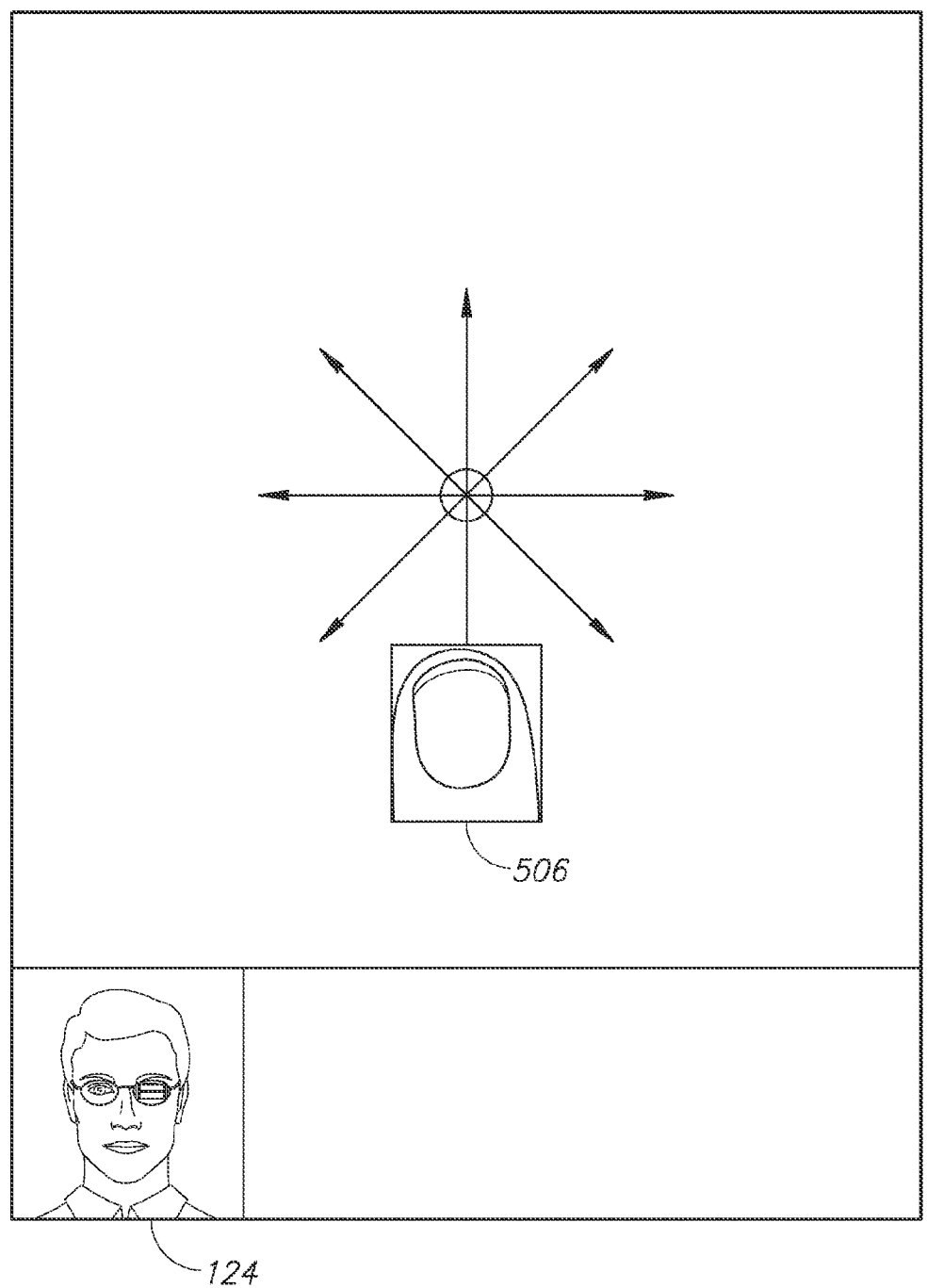
FIG. 30 illustrates a fourth screen shot of a musical wheel game measuring central acuity in accordance with an embodiment.

The advantage of this alternate scheme is that the user taps on the distortion 513 directly (see FIG. 34) without going to a second screen of arrows (see FIG. 30). Furthermore, circles of various sizes can be tested in quick succession. Thus the testing can proceed more rapidly. The limitation of this configuration is that the circle expansion and the presentation of the target must be slow relative to the subject's reaction time. The subject's reaction time must first be assessed using a superthreshold target (large distortion) that the subject is able to perceive.

A contracting circular target can also be used. An efficient implementation is a series of expanding and contracting circular targets that start at a randomly determined circle diameter. These random variation keep the test results from being skewed by player learning and expectation, and also keeps the game more interesting.

Assessment of Fixation Reliability

To test whether the subject is reliably fixing gaze on the central fixation target 500/511, the subject is asked to tap on the central fixation target when it flashes. This task encourages the subject to keep gaze on the central fixation target. This is done intermittently between the hyperacuity testing cycles. The percentage of fixation failures is monitored to determine if the test results are reliable.

Keeping of Game Score

The subject is rewarded by game score increment for correctly tapping on the distortion during the hyperacuity testing cycle or tapping on the fixation target during fixation reliability testing cycles. The number of points awarded should be larger for faster reaction to encourage faster game play. The subject is punished by game score decrement when tapping at the wrong location or failing to tap. The score and the accompanying visual and sound feedback keep the player interested. The score is meant to be a player motivator and is generally not the same as the visual test results, though they may be partially related.

Dynamic Correction of Display Size

During the game play and acuity testing, the distance between the subject's eyes and the display area (screen) of the device 100 is continuously monitored so the size and location of the peripheral visual field stimulus remains true to the specified visual angles. Thus, if the subject's eyes move closer to the device the image on display will be made smaller and if the subject's eyes move away from the device then the image on display will be made larger.

Mapping of Scotoma and Metamorphopsia

Figure 35:
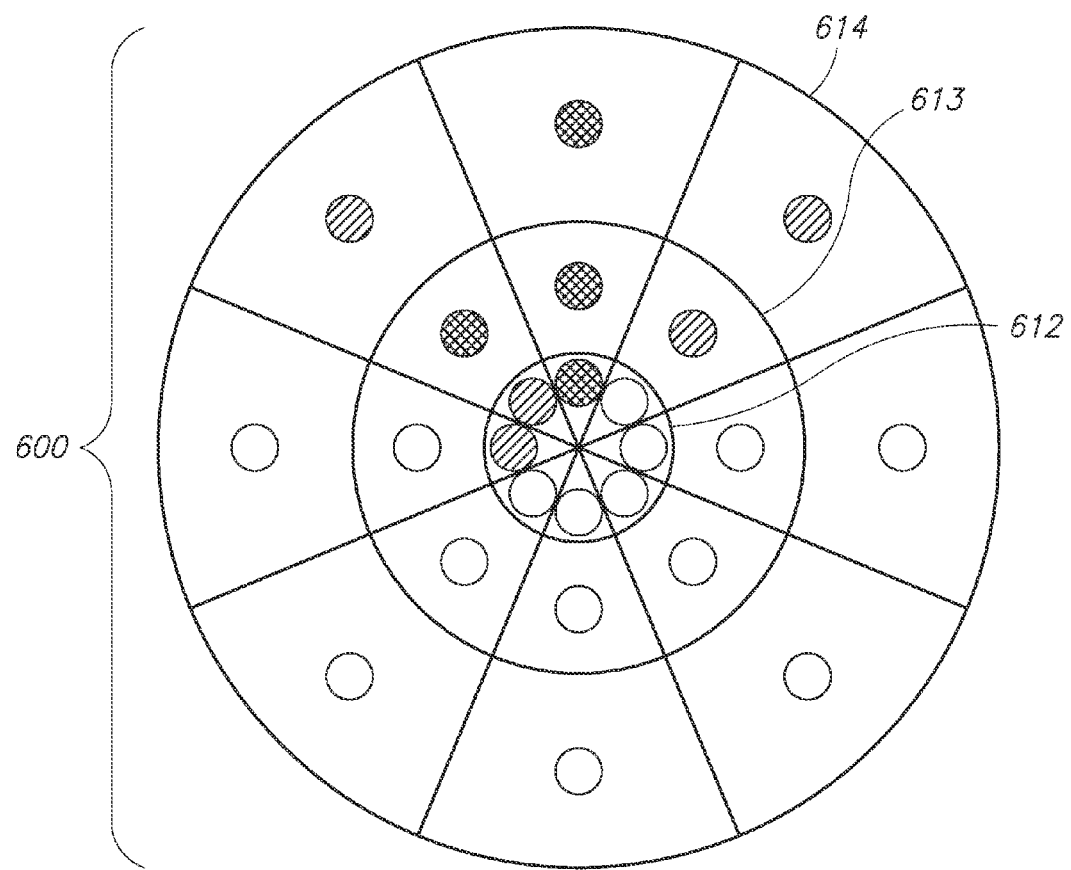
FIG. 35 illustrates a Scotoma map output from the musical wheel game.
Figure 36:
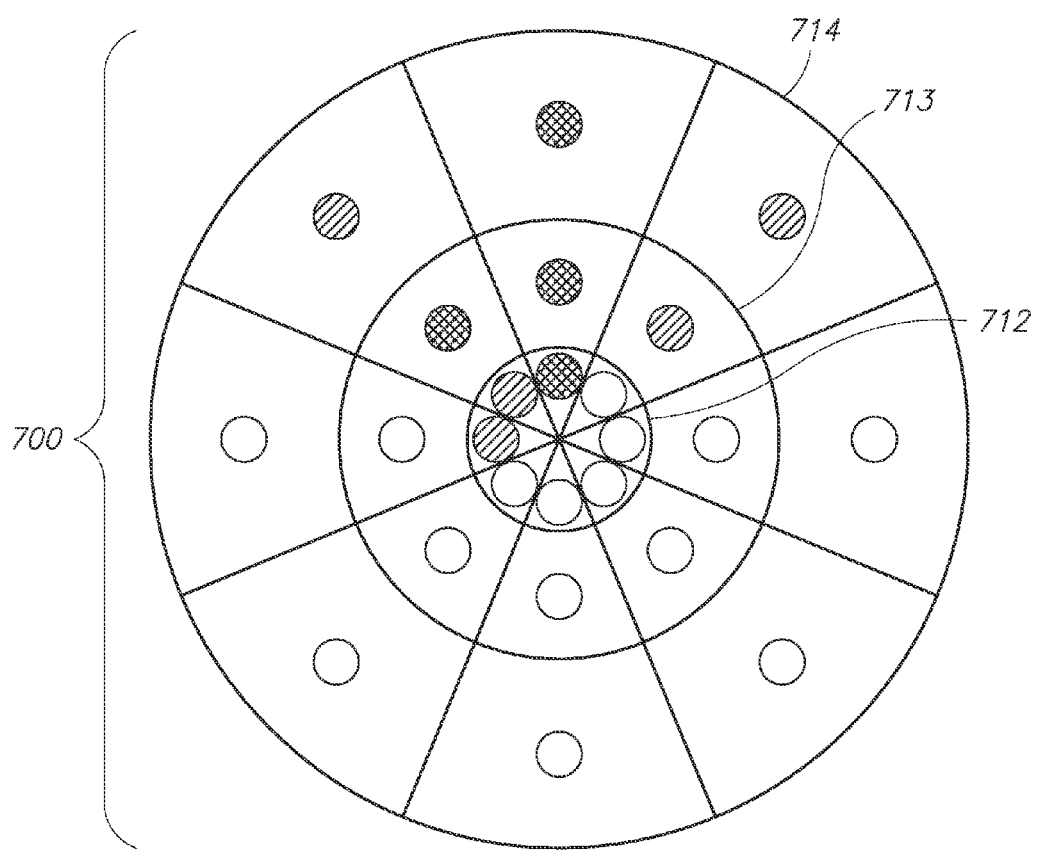
FIG. 36 illustrates Metamorphopsia map output from the musical wheel game.

The outputs of the game are a map of scotoma probability (FIG. 35) and a map of metamorphopsia probability (see FIG. 36). The dimension of the maps is preferably approximately 16°, which can be easily accommodated by tablet computers currently on the market. For example, the iPad2 has a display area that is 5.8 inches wide. This provides a maximum visual field width of +/−18 degrees at a viewing distance of 18 inches. Referring to FIG. 35, the scotoma probability map 600 is presented as a polar grid of probability values. The polar grid is divided into central region 612 spanning the central 3° visual angle (diameter), parafoveal region 613 spanning the annulus from 3° to 8° visual angle (diameter), and perifoveal region 614 spanning the annulus from 8° to 16° visual angle (diameter). The parafoveal and perifoveal annuli are each subdivided into 8 sectors. Referring to FIG. 36, the metamorphopsia map 700 is similarly divided into 3 diameters 712, 713, and 714. The probability levels are preferably displayed by easy to interpret symbols on the maps. In FIGS. 35 and 36, the unhatched circles represent <90% probability of abnormality, the linear-hatched circles represent >90% probability of abnormality, and the cross-hatched circles represent >99% probability of abnormality. More gradations or exact probability values could also be provided. The maps are preferably automatically computed by the game device computer immediately after the game so the results can be shown to the player to maintain interest in the game.

FIGS. 35 and 36 represent one preferred implementation. More or fewer angular sectors or annuli could be employed. The map division shown is preferred because the number of test locations (24) is reasonable and the sampling density is appropriately weighed with denser central sampling.

Electronic Communication to a Physician

The results of the video game tests are preferably communicated to a physician on a regular basis and whenever a new abnormality is detected. Any abrupt or gradual trend in scotoma or metamorphopsia probability is automatically computed by the game device and communicated to the physician. Alternatively, test results can be tracked and analyzed over the long term by the central computer server 168. Communication between the game device 100, central server 168, and physician occur over an electronic network 167. The physician can instruct the subject to take the test more or less frequently via the same network. If the level of scotoma and/or metamorphopsia is too severe for the standard distortion magnitude (if a majority of the map sectors show abnormality), the physician can increase the magnitude of the vernier distortion so only areas with more severe scotoma and metamorephopsia are mapped. This improves the ability to detect further increase in abnormal areas.

Advantages

The current embodiment is a video game-based preferential hyperacuity perimetry test having one or more of the following advantages over prior art:
 1. The test can be implemented on common consumer-owned hardware platforms such as a smartphone, laptop computer or a tablet computer (i.e. the iPad2). This allows more frequent testing.
 2. The target has circular symmetry around the central fixation target, thereby minimizing the temptation for subject gaze to move off center.
 3. Fixation is further assured by a task that requires the user to tap on the central fixation target periodically.
 4. The game uses action-generated sound to help hold subject attention.
 5. The pace of the game is controlled by the player.
 6. The subject's head is free to move to improve comfort. The distance between the video screen and the subject's eyes is monitored by a camera and this information is used to provide compensatory adjustment in visual stimulus size so the visual angle subtended by the stimulus remains well characterized.
 7. The ambient light level is monitored by the video camera(s) included in the apparatus of the current embodiment.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

What is claimed is:

1. A computer-implemented method for testing macular visual acuity, comprising:
   (A) displaying a fixation location indicator on a display of a computing device configured for fixation thereon by a user;
   (B) simultaneously and briefly displaying on the display a hyperacuity target arranged around the fixation location indicator, wherein a correct portion of the hyperacuity target is spaced apart from the fixation location indicator at a different distance than an other portion of the hyperacuity target;
   (C) receiving input from the user via a user input device indicating a user selection of a portion of the hyperacuity target;
   (D) determining whether the user selected the correct portion; and
   (E) recording whether the user selected the correct portion in a data storage.

2. The computer-implemented method of claim 1, wherein the correct portion is spaced farther from the fixation location indicator than the other portion of the hyperacuity target.

3. The computer-implemented method of claim 1, wherein the hyperacuity target has a symmetrical shape.

4. The computer-implemented method of claim 1, wherein the hyperacuity target comprises a plurality of targets and the correct portion is one of the plurality of targets.

5. The computer-implemented method of claim 1, wherein the hyperacuity target includes a substantially continuous shape surrounding the fixation location indicator and the correct portion is a distorted or discontinuous portion of the substantially continuous shape.

6. The computer-implemented method of claim 1, wherein the input from the user includes tapping on one of a plurality of arrows displayed on the display.

7. The computer-implemented method of claim 1, the method further comprising:
   testing visual acuity by executing a plurality of visual acuity rounds of the video game, each visual acuity round comprising steps (A)-(E); and
   generating a visual acuity map based on a user's selections during the plurality of visual acuity rounds, wherein in the visual acuity map is divided into a plurality of locations, and each of the plurality of locations is tested by at least one visual acuity round of the video game.

8. The computer-implemented method of claim 7, the method further comprising:
   obscuring part of the hyperacuity target based on the user selection in at least one of the plurality of visual acuity rounds.

9. The computer-implemented method of claim 7, wherein a size of the hyperacuity target displayed on the display is different in at least two of the plurality of visual acuity rounds.

10. The computer-implemented method of claim 7, wherein, during each of the visual acuity rounds, a characteristic of the hyperacuity target displayed on the display is dependent on the user's selection in a previous visual acuity round.

11. The computer-implemented method of claim 7, wherein the generating a visual acuity map includes generating a scotoma probability map or a metamorphosis probability map.

12. The computer-implemented method of claim 7, wherein a size of the hyperacuity target is either successively expanded or contracted in subsequent visual acuity rounds.

13. The computer-implemented method of claim 1, wherein a size of the hyperacuity target displayed on the display is dependent on an area of visual acuity being tested.

14. The computer-implemented method of claim 1, wherein the input from the user includes tapping on the hyperacuity target displayed on the display.

15. The computer-implemented method of claim 1, further comprising:
   providing an instruction to the user to either increase or decrease his or her distance from the display based on a distance between the display of the computing device and the user.

16. The computer-implemented method of claim 1, further comprising:
   adjusting a brightness level of the display dependent on an ambient light level.

17. The computer-implemented method of claim 1, further comprising:
   transmitting data relating to the user's visual acuity to an external computing device.

18. The computer-implemented method of claim 1, wherein determining whether the user selected the correct portion includes determining (I) a visual acuity score based on whether the user selected the correct portion; and (II) a game score based on a reaction time between when the hyperacuity target is displayed and when the input from the user is received.

19. A system for testing macular visual acuity, comprising:
   a display;
   a user input device; and
   a computer coupled to the display and the user input device, and configured to (A) display a fixation location indicator on the display, (B) simultaneously and briefly display on the display an hyperacuity target arranged around the fixation location indicator, wherein a correct portion of the hyperacuity target is spaced apart from the fixation location indicator at a different distance than an other portion of the hyperacuity target, (C) receive input from the user via the user input device indicating a user selection of a portion of the hyperacuity target, and (D) determine whether the user selected the correct portion.

20. The system of claim 19, wherein the correct portion is spaced farther from the fixation location indicator than the other portion of the hyperacuity target.

21. The system of claim 19, wherein the hyperacuity target has a symmetrical shape.

22. The system of claim 19, wherein the computer is further configured to (E) record whether the user selected the correct portion in a data storage.

23. The system of claim 22, wherein the computer is further configured to:
   execute a plurality of visual acuity rounds of the video game, each visual acuity round comprising steps (A)-(E); and
   generate a visual acuity map based on the user's selections during the plurality of visual acuity rounds, wherein in the visual acuity map is divided into a plurality of locations, and each of the plurality of locations is tested by at least one visual acuity round of the video game.

24. The system of claim 23, wherein, when generating the visual acuity map, the computer is configured to generate a scotoma probability map or a metamorphosis probability map.

25. A non-transitory computer-readable medium encoded with computer executable instructions, which when executed by a processor, causes the processor to perform a method comprising:
(A) displaying a fixation location indicator on a display of a computing device configured for fixation thereon by a user;
(B) simultaneously and briefly displaying on the display an hyperacuity target arranged around the fixation location indicator, wherein a correct portion of the hyperacuity target is spaced apart from the fixation location indicator at a different distance than an other portion of the hyperacuity target;
(C) receiving input from the user via a user input device of the computing device indicating a user selection of a portion of the hyperacuity target;
(D) determining whether the user correctly selected the correct portion; and
(E) assessing the user's visual acuity based on the selection of the user.

26. The non-transitory computer-readable medium of claim 25, wherein, in the simultaneously and briefly displaying, the correct portion is spaced farther from the fixation location indicator than the other portion of the hyperacuity target.

27. The non-transitory computer-readable medium of claim 25, wherein, in the simultaneously and briefly displaying, the hyperacuity target has a symmetrical shape.

28. The non-transitory computer-readable medium of claim 25, wherein, in the simultaneously and briefly displaying, the hyperacuity target comprises a plurality of targets and the correct portion is one of the plurality of targets.

29. The non-transitory computer-readable medium of claim 25, wherein, in the simultaneously and briefly displaying, the hyperacuity target includes a substantially continuous shape surrounding the fixation location indicator and the correct portion is a distorted or discontinuous portion of the substantially continuous shape.

30. The non-transitory computer-readable medium of claim 25, the method further comprising:
testing visual acuity by executing a plurality of visual acuity rounds of the video game, each visual acuity round comprising steps (A)-(E); and
generating a visual acuity map based on the user's selections during the plurality of visual acuity rounds, wherein in the visual acuity map is divided into a plurality of locations, and each of the plurality of locations is tested by at least one visual acuity round of the video game.

31. The non-transitory computer-readable medium of claim 30, wherein the generating a visual acuity map includes generating a scotoma probability map or a metamorphosis probability map.

32. The non-transitory computer-readable medium of claim 25, wherein determining whether the user selected the correct portion includes determining (I) a visual acuity score based on whether the user selected the correct portion; and (II) a game score based on a reaction time between when the hyperacuity target is displayed and when the input from the user is received.

33. A method of distributing data adapted to be stored on a non-transitory computer-readable medium, the data including computer executable instructions, which when executed by a processor, cause the processor to perform a method for testing macular visual acuity comprising the steps of:
(A) displaying a fixation location indicator on a display of a computing device configured for fixation thereon by a user;
(B) simultaneously and briefly displaying on the display a hyperacuity target arranged around the fixation location indicator, wherein a correct portion of the hyperacuity target is spaced apart from the fixation location indicator at a different distance than an other portion of the hyperacuity target;
(C) receiving input from the user via a user input device indicating a user selection of a portion of the hyperacuity target;
(D) determining whether the user selected the correct portion; and
(E) recording whether the user selected the correct portion in a data storage.

34. The method of distributing data of claim 33, wherein, in the simultaneously and briefly displaying, the correct portion is spaced farther from the fixation location indicator than the other portion of the hyperacuity target.

35. The method of distributing data of claim 33, wherein, in the simultaneously and briefly displaying, the hyperacuity target has a symmetrical shape.

36. The method of distributing data of claim 33, the method for testing macular visual acuity further comprising:
testing visual acuity by executing a plurality of visual acuity rounds of the video game, each visual acuity round comprising steps (A)-(E); and
generating a visual acuity map based on the user's selections during the plurality of visual acuity rounds, wherein in the visual acuity map is divided into a plurality of locations, and each of the plurality of locations is tested by at least one visual acuity round of the video game.

* * * * *